US011351374B2

(12) United States Patent
Mowery et al.

(10) Patent No.: US 11,351,374 B2
(45) Date of Patent: *Jun. 7, 2022

(54) SYSTEM AND METHOD FOR OCULAR STIMULATION

(71) Applicant: i-Lumen Scientific, Inc., Bloomington, MN (US)

(72) Inventors: Blair P. Mowery, College Grove, TN (US); Marshall T. Masko, Minnetonka, MN (US); John B. Jarding, Rapid City, SD (US); Gary A. Tapp, Plymouth, MN (US)

(73) Assignee: i-Lumen Scientific, Inc., Bloomington, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 17/460,047

(22) Filed: Aug. 27, 2021

(65) Prior Publication Data
US 2021/0387000 A1 Dec. 16, 2021

Related U.S. Application Data

(63) Continuation of application No. 17/079,287, filed on Oct. 23, 2020, now Pat. No. 11,103,705, which is a (Continued)

(51) Int. Cl.
*A61N 1/36* (2006.01)
*A61N 1/04* (2006.01)

(52) U.S. Cl.
CPC ....... *A61N 1/36046* (2013.01); *A61N 1/0456* (2013.01); *A61N 1/0476* (2013.01); (Continued)

(58) Field of Classification Search
CPC ............. A61N 1/36046; A61N 1/0456; A61N 1/0476; A61N 1/0496; A61N 1/36014; A61N 1/36031; A61N 1/36034
See application file for complete search history.

(56) References Cited

U.S. PATENT DOCUMENTS 3,376,870 A 4/1968 Yamamoto et al.
3,669,119 A 6/1972 Symmes
(Continued)

FOREIGN PATENT DOCUMENTS

WO WO_2014110575 7/2014
WO WO_2014142970 9/2014

OTHER PUBLICATIONS

Wrobel, et al., "Therapy for Retinal Degeneration", "Retina Today", Oct. 2011, pp. 80-81.
(Continued)

*Primary Examiner* — Mallika D Fairchild
(74) *Attorney, Agent, or Firm* — Charles A. Lemaire; Jonathan M. Rixen; Lemaire Patent Law Firm, P.L.L.C.

(57) ABSTRACT

Devices and methods to deliver microcurrent stimulation therapy to the human body, when connected to a microstimulation current-generating apparatus. The method of applying microcurrent stimulation therapy to key points around the eye for treatment of problems such as macular degeneration, retinitis pigmentosa, glaucoma, optic neuritis and other eye-related or nerve-related conditions, as well as other diseases, such as Bell's Palsy, requiring localized stimulation to the eyes and/or on other body parts.

20 Claims, 10 Drawing Sheets

Related U.S. Application Data continuation of application No. 16/943,814, filed on Jul. 30, 2020, now Pat. No. 11,065,447, which is a continuation of application No. 16/851,853, filed on Apr. 17, 2020, now Pat. No. 10,874,858, which is a continuation of application No. 16/551,672, filed on Aug. 26, 2019, now Pat. No. 10,682,514, which is a continuation of application No. 15/759,515, filed as application No. PCT/US2016/051550 on Sep. 13, 2016.

(60) Provisional application No. 62/365,838, filed on Jul. 22, 2016, provisional application No. 62/283,870, filed on Sep. 15, 2015, provisional application No. 62/283,871, filed on Sep. 15, 2015.

(52) U.S. Cl.
CPC ....... *A61N 1/0496* (2013.01); *A61N 1/36014* (2013.01); *A61N 1/36031* (2017.08); *A61N 1/36034* (2017.08)

(56) References Cited

U.S. PATENT DOCUMENTS

| | | | |
|---|---|---|---|
| 4,018,218 A | 4/1977 | Carlson et al. | |
| 4,989,605 A | 2/1991 | Rossen | |
| 5,522,864 A | 6/1996 | Wallace et al. | |
| 5,843,147 A | 12/1998 | Testerman et al. | |
| 6,035,236 A | 3/2000 | Jarding et al. | |
| 6,275,735 B1 | 8/2001 | Jarding et al. | |
| 6,350,275 B1 | 2/2002 | Vreman et al. | |
| 6,445,955 B1 | 9/2002 | Michelson et al. | |
| 6,587,728 B2 | 7/2003 | Fang et al. | |
| 6,636,754 B1 | 10/2003 | Baura et al. | |
| 6,792,314 B2 | 9/2004 | Byers et al. | |
| 6,993,387 B2 | 1/2006 | Connelly et al. | |
| 7,062,319 B1 | 6/2006 | Ihme et al. | |
| 7,069,084 B2 | 6/2006 | Yee | |
| 7,158,834 B2 | 1/2007 | Paul, Jr. | |
| 7,215,989 B1 | 5/2007 | Burks | |
| 7,251,528 B2 | 7/2007 | Harold | |
| 7,326,181 B2 | 2/2008 | Katims | |
| 7,771,342 B2 | 8/2010 | Rademacher et al. | |
| 8,116,841 B2 | 2/2012 | Bly et al. | |
| 8,494,625 B2 | 7/2013 | Hargrove | |
| 8,554,324 B2 | 10/2013 | Brocke | |
| 8,560,077 B2 | 10/2013 | Feinstein | |
| 8,639,345 B2 | 1/2014 | Eipper et al. | |
| 8,731,657 B1 | 5/2014 | Shambayati et al. | |
| 8,781,594 B2 | 7/2014 | Lindenthaler | |
| 8,958,883 B2 | 2/2015 | Mueller et al. | |
| 9,061,148 B2 | 6/2015 | Bachinski et al. | |
| 9,199,080 B2 | 12/2015 | Gekeler et al. | |
| 9,308,363 B2 | 4/2016 | Goroszeniuk et al. | |
| 9,474,446 B2 | 10/2016 | Amann et al. | |
| 9,510,972 B2 | 12/2016 | Badawi | |
| 9,566,427 B2 | 2/2017 | Wagner | |
| 9,675,794 B2 | 6/2017 | Miller | |
| 9,719,977 B2 | 8/2017 | Korb et al. | |
| 9,724,230 B2 | 8/2017 | Badawi | |
| 9,999,766 B2 | 6/2018 | Elliott | |
| 10,016,600 B2 | 7/2018 | Creasey et al. | |
| 10,376,691 B2 | 8/2019 | De Toni et al. | |
| 10,456,579 B2 | 10/2019 | Salazar | |
| 10,695,219 B2 | 6/2020 | Herchman et al. | |
| 10,973,680 B2 | 4/2021 | Badawi et al. | |
| 11,007,367 B2 | 5/2021 | O'Clock | |
| 2002/0026225 A1 | 2/2002 | Segal | |
| 2005/0137649 A1 | 6/2005 | Paul, Jr. | |
| 2008/0171929 A1 | 7/2008 | Katims | |
| 2009/0048642 A1 | 2/2009 | Goroszeniuk | |
| 2010/0298863 A1 | 11/2010 | Hindinger et al. | |
| 2011/0081333 A1 | 4/2011 | Shantha et al. | |
| 2015/0018927 A1 | 1/2015 | Warschewske | |
| 2017/0036009 A1 | 2/2017 | Hughes et al. | |
| 2018/0325729 A1 | 11/2018 | Rynerson | |
| 2019/0046794 A1 | 2/2019 | Goodall et al. | |

OTHER PUBLICATIONS

Chaikin, et al., "Microcurrent stimulation in the treatment of dry and wet macular degeneration", "Clinical Ophthalmology", Dec. 2015, pp. 2345-2353, vol. 2015:9.

Fujikado, et al., "Effect of Transcorneal Electrical Stimulation in Patients with Nonarteritic Ischemic Optic Neuropathy or Traumatic Optic Neuropathy", "Jpn J Ophthalmol", May-Jun. 2006, pp. 266-273, vol. 50.

Morimoto, et al., "Evaluation of residual retinal function by pupillary constrictions and phosphenes using transcorneal electrical stimulation in patients with retinal degeneration", Mar. 21, 2006, pp. 1283-1292, vol. 244.

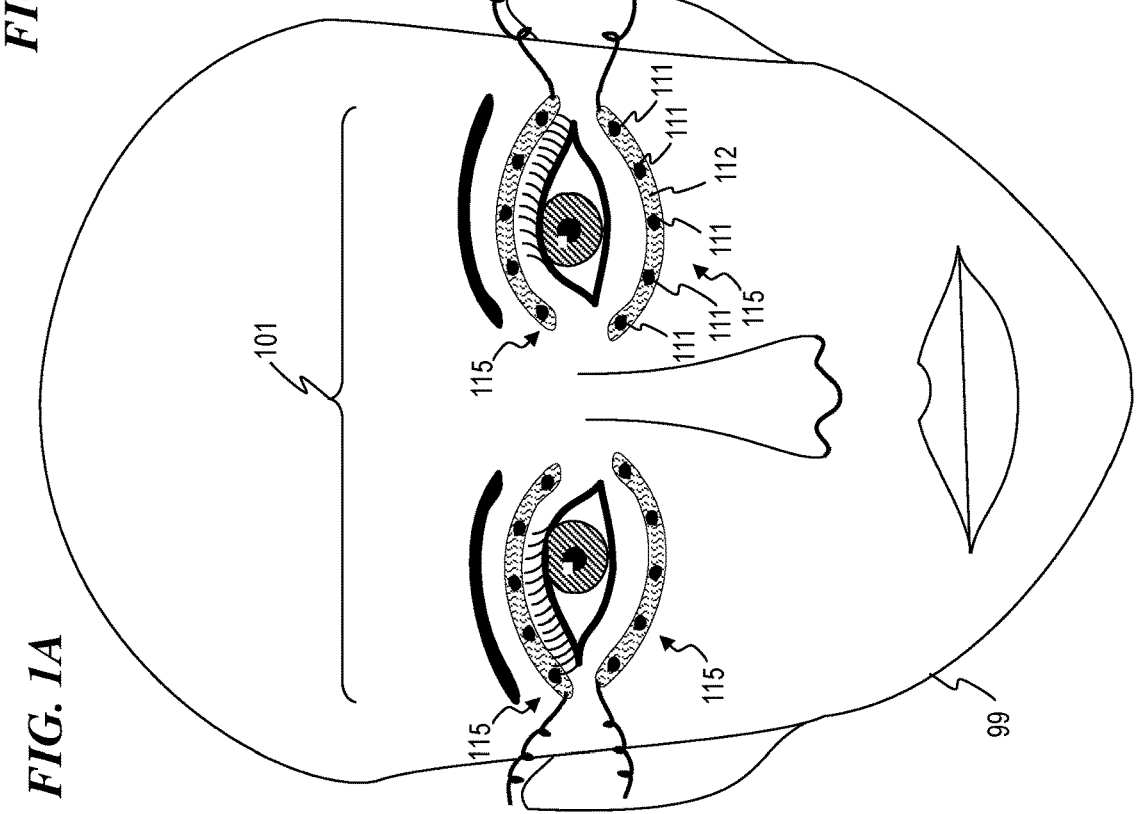
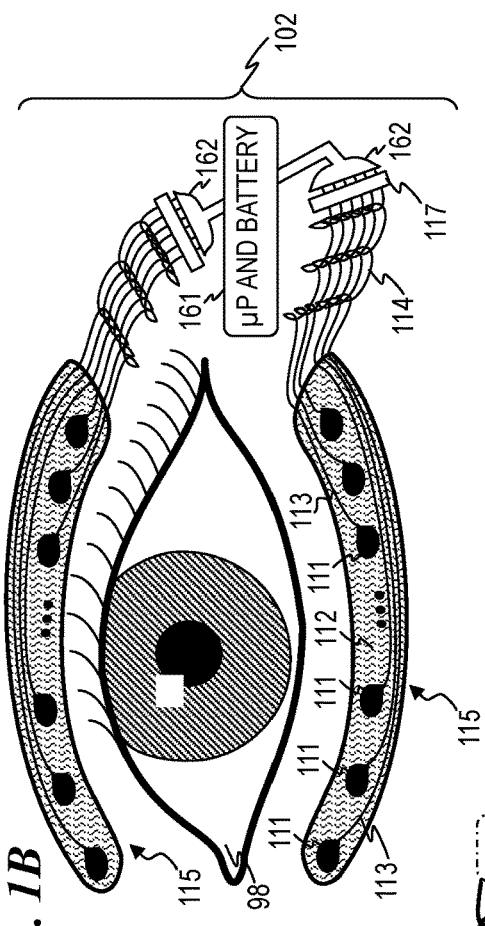
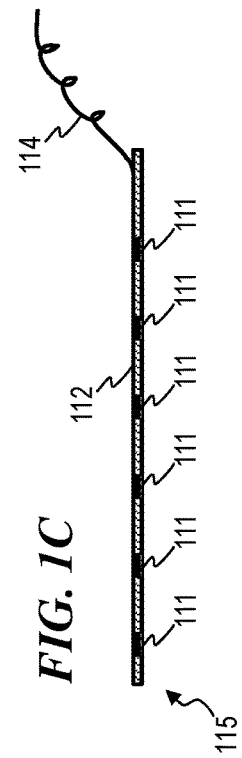
FIG. 1A
FIG. 1B
FIG. 1C

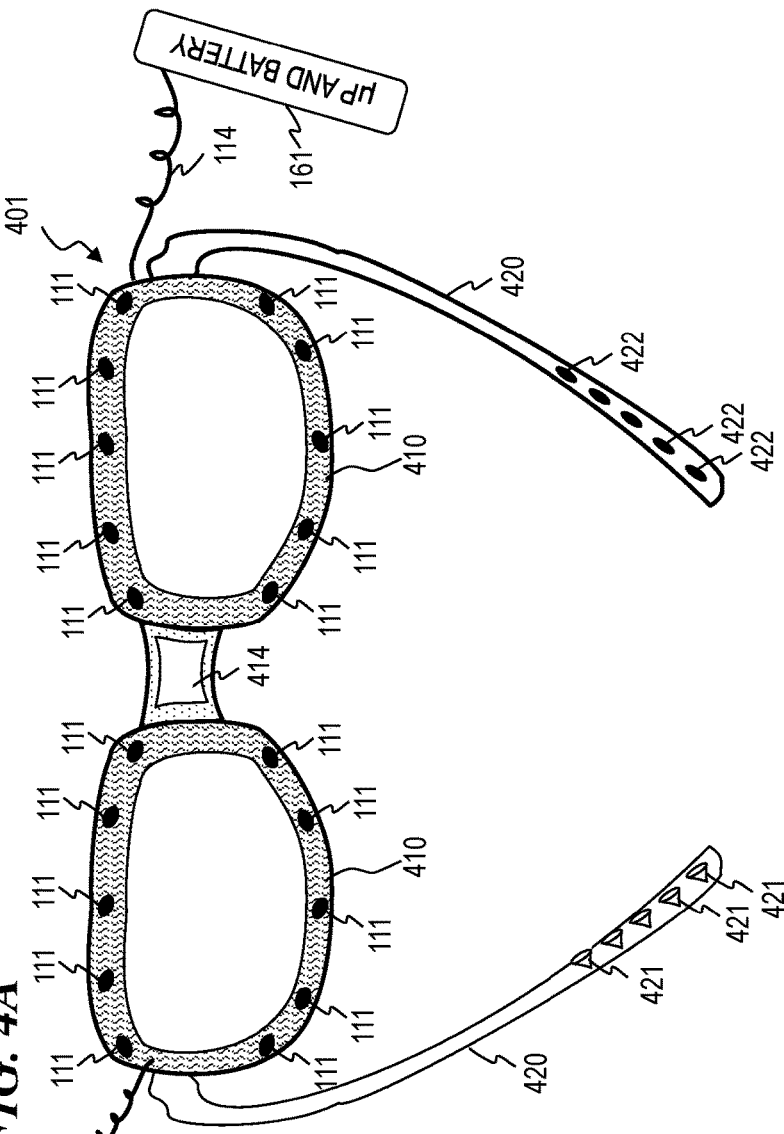
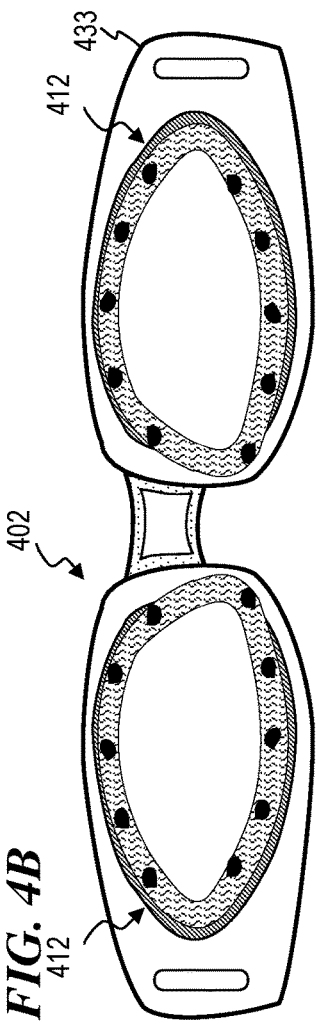
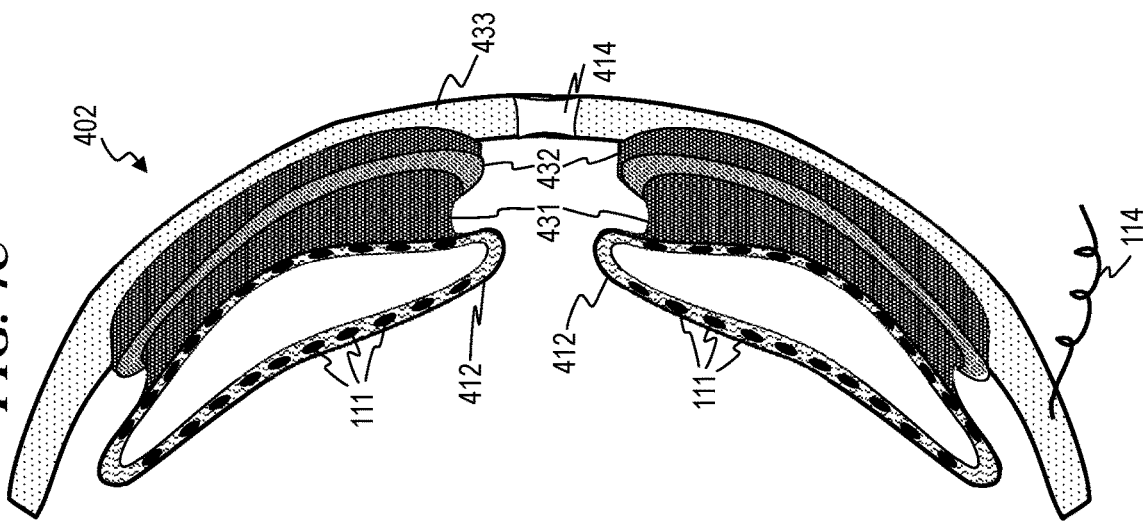

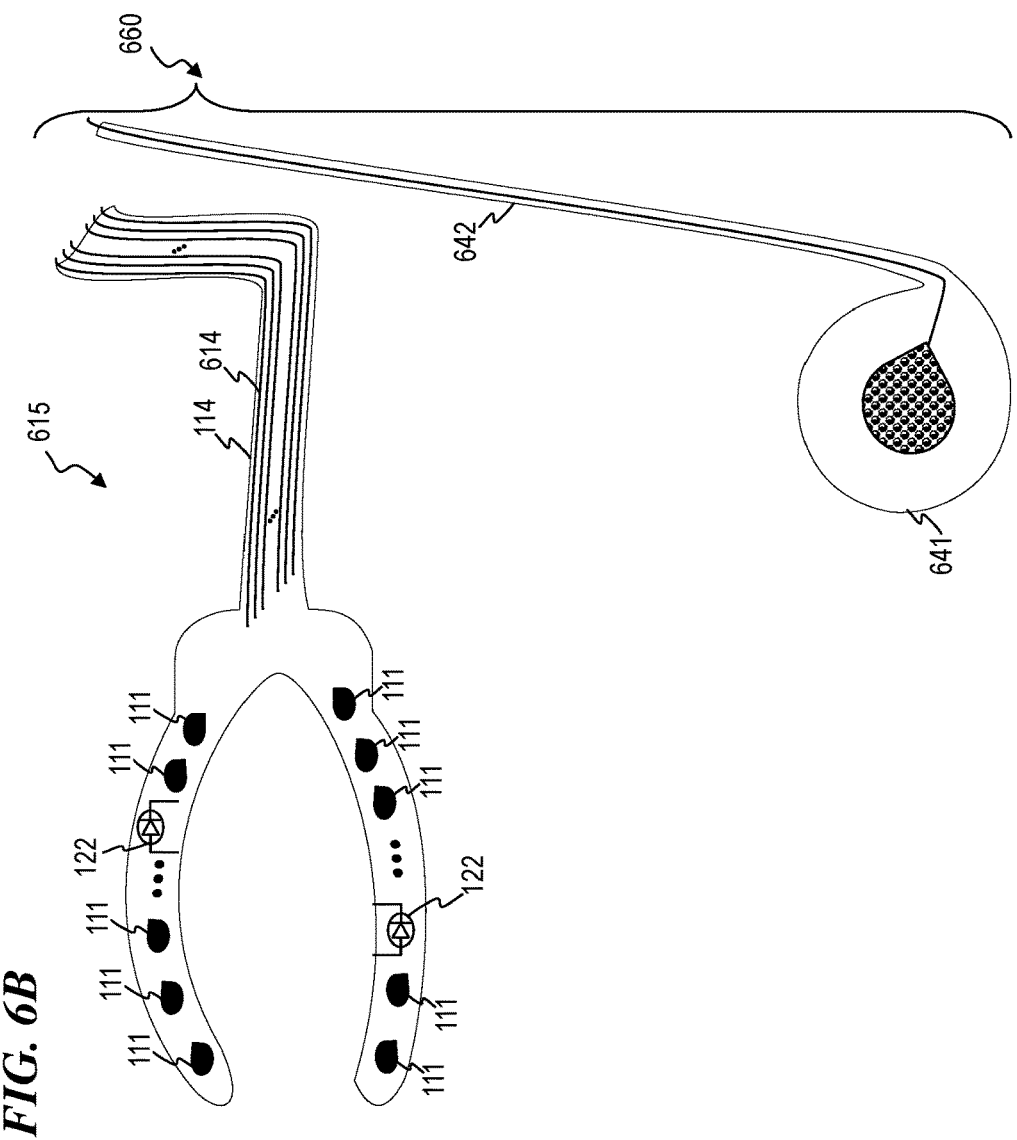
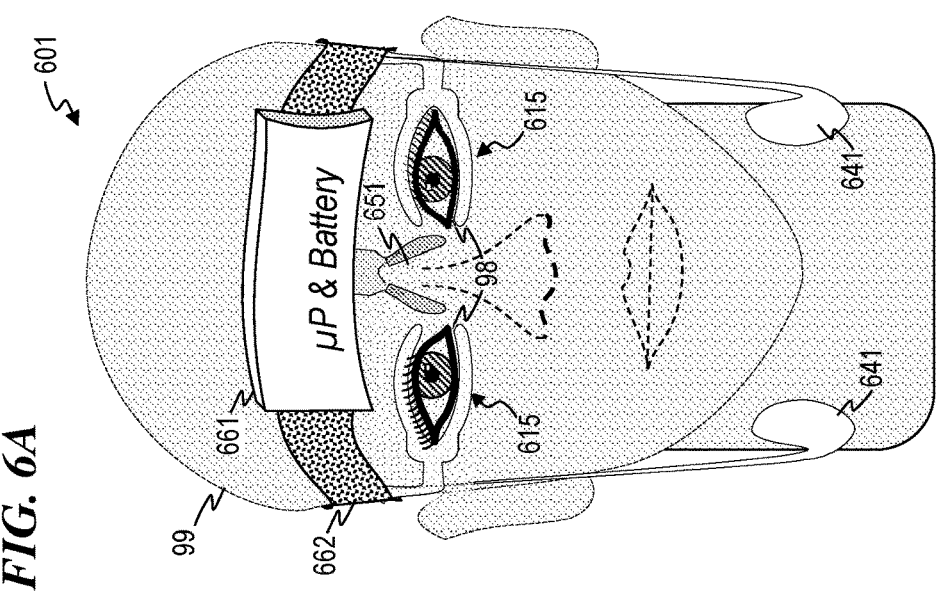
FIG. 6B
FIG. 6A

SYSTEM AND METHOD FOR OCULAR STIMULATION

CROSS-REFERENCE TO RELATED APPLICATIONS

This application is a continuation application of U.S. patent application Ser. No. 17/079,287, filed Oct. 23, 2020 (which issued as U.S. Pat. No. 11,103,705 on Aug. 31, 2021), which is a continuation application of U.S. patent application Ser. No. 16/943,814, filed Jul. 30, 2020 (which issued as U.S. Pat. No. 11,065,447), which is a continuation application of U.S. patent application Ser. No. 16/851,853 filed Apr. 17, 2020 (which issued as U.S. Pat. No. 10,874,858), which is a continuation application of U.S. patent application Ser. No. 16/551,672 filed Aug. 26, 2019 (which issued as U.S. Pat. No. 10,682,514 on Jun. 16, 2020), which is continuation application of U.S. patent application Ser. No. 15/759,515 filed Mar. 12, 2018 (which issued as U.S. Pat. No. 10,391,312 on Aug. 27, 2019), which is a national-phase filing of, and claims priority benefit of, PCT Patent Application No. PCT/US2016/051550, filed Sep. 13, 2016 by Blair P. Mowery et al. and titled "Apparatus and method for ocular microcurrent stimulation therapy," which claims priority benefit, including under 35 U.S.C. § 119(e), of U.S. Provisional Patent Application No. 62/283,870, filed Sep. 15, 2015 by Mowery et al., titled "Appliance for microcurrent stimulation therapy using a disposable material afixed to the upper and lower eye lid & other body parts," U.S. Provisional Patent Application No. 62/283,871, filed Sep. 15, 2015 by Masko et al., titled "Apparatus for a method of application of microcurrent stimulation therapy, consisting of a goggle device affixed to & encircling the upper and/or lower eyelids, as well as other body parts," and U.S. Provisional Patent Application No. 62/365,838, filed Jul. 22, 2016 by Tapp et al., titled "Appliance for micro-current stimulation," each of which is incorporated herein by reference in its entirety.

FIELD OF THE INVENTION

The present invention relates to devices and methods to electrically stimulate animal tissue, and in particular to a microstimulation electrode appliance that delivers microcurrent stimulation therapy to the human body, when connected to a microstimulation current generating apparatus. The present invention further relates to a way of applying microcurrent stimulation therapy to key points around the eye for treatment of diseases such as macular degeneration, retinitis pigmentosa, glaucoma, optic neuritis, optic neuropathy, diabetic retinopathy, macular edema, papilledema, and other eye-related or nerve-related maladies, as well as other diseases, such as Bell's Palsy, requiring localized stimulation on other body parts.

BACKGROUND OF THE INVENTION

Chronic pain is a problem for millions of individuals throughout the world. One method of treating such pain is to provide microcurrent stimulation around or near the areas where the pain is occurring. Microcurrent, which typically is defined as current below one (1) milliamp, can provide rapid and long-lasting pain relief for a wide variety of pain syndromes. Generally, microcurrent stimulation therapy typically includes applying a current in the range of about 20 to about 300 microamps (~20 to ~300 µA) to the affected area. The current blocks neuronal transmission of pain signals and stimulates the release of endorphins to help relieve the pain in chronic and acute pain patients and suppress the inflammatory response.

In addition to chronic pain relief, microcurrent therapy is being used to treat a number of visual diseases, including macular degeneration, retinitis pigmentosa, macular edema, glaucoma, optic neuritis, Bell's Palsy and other diseases. It is believed, through secondary literature, that this microcurrent treatment stimulates blood flow, increases ATP (adenosine triphosphate) at the cellular level, and enhances cellular permeability. Further, it is believed such stimulation can re-establish functional neural pathways for muscle and brain, as well as for blood vessel and brain.

Age-related macular degeneration (AMD) is a very common eye disease, affecting more people than glaucoma. Macular degeneration is the most frequent cause of blindness for patients aged 60 and above in the United States, and is estimated to affect over 10 million Americans. (Source: National Health Institute). Macular degeneration results in the deterioration of various retinal tissues in the region of the macula, the central, most sensitive light-sensing area of the retina responsible for detailed central vision. Impaired blood circulation in the central retina, with partial to full corresponding vision loss, is a typical consequence of macular degeneration.

Because there is currently no approved treatment for dry AMD, little research has been done on the market potential. There is, however, significant data on the large numbers of people affected by AMD, which is estimated to cause about 8.7% of blindness and low vision globally. According to a report from the World Health Organization, "AMD is the primary cause of blindness in the developed countries and the third leading cause worldwide." The prevalence of AMD in Europe is estimated to be: 16.3 million people (excluding southeastern and eastern Europe), and in the United States 10.2 million people. Further, this increases to a combined total of 41 million cases when adding in Canada, Australia, New Zealand, Russia, and Japan. Ninety percent (90%) of these cases are dry AMD for which there is no currently approved treatment to restore vision.

Approximately 25% of the population in the target markets (aged 65 to 75 years old) has AMD, and this increases to 35% for ages 75 and older. Within the next 10 to 20 years, as "baby boomers" reach their mid-sixties and older, the prevalence of the disease is projected to dramatically increase. In a study funded by the U.S. Centers for Disease Control and Prevention, researchers reported that as many as 9.1 million people in the U.S. had AMD in 2010 and 17.8 million would have it by 2050 (Rein et al., "Forecasting age-related macular degeneration through the year 2050: the potential impact of new treatments," Arch Ophthalmol. 2009 April; 127(4):533-40. doi: 10.1001/archophthalmol.2009.58).

The U.S. spends $2.7 trillion in healthcare each year, of which eye care represents roughly three percent or $60-$70 billion of the total. According to Eurostat, the European Union (EU) spends 45.7% of that amount or about $1.23 trillion. Expenditures for eye care are growing at six percent annually. According to the National Institute for Health (NIH), it is expected to continue to grow at least six percent over the next several decades, driven by the aging population.

Macular degeneration causes about $184 billion in lost productivity each year and approximately $51 billion is spent treating macular degeneration each year in the United States. Ninety percent (90%) of macular degeneration cases are the "dry" or non-bleeding form, termed "atrophic AMD" and about 10% of cases are the "wet" or bleeding form, termed "exudative AMD".

U.S. Pat. No. 7,158,834 issued to Paul, Jr. on Jan. 2, 2007 with the title "Method and apparatus for performing microcurrent stimulation (MSC) therapy," and is incorporated herein by reference. U.S. Pat. No. 7,158,834 describes a method and apparatus for providing microcurrent stimulation (MSC) therapy. U.S. Pat. No. 7,158,834 states: it has been determined that the application of microcurrent signals at particular frequencies to the eye for particular periods of time stabilizes and even improves conditions of macular degeneration and other ocular diseases.

U.S. Pat. No. 8,731,657 issued to Shambayati, et al. on May 20, 2014 with the title "Multi-mode microcurrent stimulus system with safety circuitry and related methods," and is incorporated herein by reference. U.S. Pat. No. 8,731,657 describes a microcurrent stimulation device with a power supply, two or more electrodes electronically coupled to the power supply, a microcontroller configured to generate an electromagnetic waveform, an impedance measurement module configured to measure electrical impedance of one or more biological tissues between the two or more electrodes. A first safety circuit monitors electric current flow through one or more components of the microcurrent stimulation device and interrupts electric current flow if the electric current flow through the one or more components is above a predetermined level. A second safety circuit interrupts electric current flow through the one or more components if a firmware failure occurs.

U.S. Pat. No. 8,116,841 issued to Bly, et al. on Feb. 14, 2012 with the title "Adherent device with multiple physiological sensors," and is incorporated herein by reference. U.S. Pat. No. 8,116,841 describes an adherent device to monitor a patient for an extended period comprises a breathable tape. The breathable tape comprises a porous material with an adhesive coating to adhere the breathable tape to a skin of the patient. At least one electrode is affixed to the breathable tape and capable of electrically coupling to a skin of the patient. A printed circuit board is connected to the breathable tape to support the printed circuit board with the breathable tape when the tape is adhered to the patient. Electronic components electrically are connected to the printed circuit board and coupled to the at least one electrode to measure physiologic signals of the patient. A breathable cover and/or an electronics housing is disposed over the circuit board and electronic components and connected to at least one of the electronics components, the printed circuit board or the breathable tape.

U.S. Pat. No. 7,326,181 issued to Katims on Feb. 5, 2008 with the title "Nervous tissue stimulation device and method," and is incorporated herein by reference. U.S. Pat. No. 7,326,181 describes a method using a precisely controlled, computer programmable stimulus for neuroselective tissue stimulation that does not leave a sufficient voltage or electrical artifact on the tissue being stimulated that would interfere or prevent a monitoring system from recording the physiological response is utilized to evaluate the physiological conduction of the tissue being studied. A computer controls both the waveform, duration and intensity of the stimulus. An output trigger to the nerve response recording component controls the timing of its operation. A neuroselective nervous tissue response latency and amplitude may be determined. The computer controlled stimulus may also be administered for therapeutic purposes.

U.S. Pat. No. 7,215,989 issued to Burks on May 8, 2007 with the title "Multiple electrode assembly," and is incorporated herein by reference. U.S. Pat. No. 7,215,989 describes multiple electrode assemblies that provide an electrical connection between a patient's body and monitoring equipment. A multiple electrode assembly requires only half as many assemblies as a conventional single electrode assembly to attach a patient to multiple pieces of equipment. Less time is required to attach the patient to the monitoring equipment. There is less patient discomfort since fewer assemblies are attached to the patient. The placement of fewer assemblies also leads to a reduced cost. The assemblies can take on a number of different shapes and lead attachment configurations to accommodate a wide range of monitoring functions.

U.S. Pat. No. 7,062,319 issued to Ihme, et al. on Jun. 13, 2006 with the title "Method and arrangement for determining suitable treatment frequency and/or intensity," and is incorporated herein by reference. U.S. Pat. No. 7,062,319 describes a method and arrangement for determining a suitable treatment frequency and/or intensity of a treatment signal used in electrical treatment. In the method, a stimulating electrical signal is directed to an object to produce different reaction types in the object at different intensities of the stimulating electrical signal. For at least three different reaction types, the intensity of the stimulating electrical signal at which a reaction type occurred is stored. The electrical signal intensities stored for the different reaction types at least at three different frequencies are compared with reference values and the frequency and/or signal intensity at which the signal intensity deviates sufficiently from one or more reference values is determined. The method utilizes the frequency and/or signal intensity found in the process in determining the suitable treatment frequency and/or signal intensity.

U.S. Pat. No. 6,636,754 issued to Baura et al. on Oct. 21, 2003 with the title "Apparatus and method for determining cardiac output in a living subject," and is incorporated herein by reference. U.S. Pat. No. 6,636,754 describes an improved apparatus and method for determining the cardiac output of a living subject. Their improved apparatus generally comprises one or more electrode assemblies or patches affixed to the skin of the subject in the vicinity of the thoracic cavity. The terminals of each electrode patch are in contact with an electrolytic gel, and are spaced a predetermined distance from one another within the patch. This predetermined spacing allows for more consistent measurements, and also allows for the detection of a loss of electrical continuity between the terminals of the patch and their associated electrical connectors in the clinical environment. The method generally comprises generating and passing a stimulation current through the terminals and the thoracic cavity of the subject, and measuring the impedance as a function of time. This impedance is used to determine cardiac muscle stroke volume, which is then used in conjunction with the subject's cardiac rate (also detected via the electrode patches) to determine cardiac output. A method of detecting a loss of electrical continuity in one or more of the terminals of the electrode patch is also disclosed.

U.S. Pat. No. 6,035,236 issued to Jarding, et al. on Mar. 7, 2000 with the title "Methods and apparatus for electrical microcurrent stimulation therapy," and is incorporated herein by reference. U.S. Pat. No. 6,035,236 describes an apparatus for supplying an electrical signal to a body part in order to provide microcurrent stimulation therapy to the body part. The apparatus preferably comprises a first sweep wave or sweep frequency signal generator configured to generate a first sweep wave signal, a buffer amplifier circuit configured to receive the first sweep wave signal from the first sweep signal generator and amplify and buffer the sweep wave signal creating a buffered sweep wave signal. In addition, the apparatus preferably includes a current limiting circuit configured to receive the buffered sweep wave signal from the buffer amplifier circuit and limit the amount of current supplied to the body part. Finally, the apparatus preferably comprises a probe for applying the sweep wave signal to the body part. The apparatus may further comprise a second signal generator for generating a second signal which may comprise either a sweep wave signal or a non-sweep wave signal. The apparatus also will include a signal combining circuit configured to receive the first and second signals from the first and second signal generators and combine the first and second signals into a composite sweep wave signal.

U.S. Pat. No. 6,275,735 issued to Jarding, et al. on Aug. 14, 2001 with the title "Methods and apparatus for electrical microcurrent stimulation therapy," and is incorporated herein by reference. U.S. Pat. No. 6,275,735 describes a method and apparatus for providing microcurrent stimulation therapy to a body part is disclosed. In one embodiment, a method allows digital control of the modulation frequency of the microcurrent signal. The method includes receiving a first digital data word which is used to produce a first frequency related to the first digital data word, whereupon, a first microcurrent signal at the first frequency is applied to the body part. A second digital data word is received and used to produce a second frequency related to the second digital data word. A second microcurrent signal at the second frequency is applied to the body part. In another embodiment, a method allows direct digital synthesis of the microcurrent stimulation signal. A first digital data word is used to produce a first analog voltage which is applied to the body part. A second digital data word is used to produce a second analog voltage which is also applied to the body part, where the first analog voltage is different from the second analog voltage. In yet another embodiment, an apparatus for providing microcurrent stimulation therapy includes a digital-to-analog converter, a controller and a plurality of data words. The controller is coupled to the digital-to-analog converter and supplies the digital-to-analog converter with digital data words in order to generate an electrical signal for the microcurrent stimulation therapy.

U.S. Patent Publication 2005/0137649 by Paul, Jr. published on Jun. 23, 2005 with the title "Method and apparatus for performing microcurrent stimulation (MSC) therapy," and is incorporated herein by reference. Patent Publication 2005/0137649 describes a method and apparatus for providing microcurrent stimulation (MSC) therapy, and asserted: it has been determined that the application of microcurrent signals at particular frequencies to the eye for particular periods of time stabilizes and even improves conditions of macular degeneration and other ocular diseases and that experimental data from clinical trials shows that results of persons who underwent therapy are at least better than placebo, and that the therapy is safe and efficacious. Patent Publication 2005/0137649 continued: experimental data from clinical trials showed that approximately 98% of the patients who underwent the MCS therapy of the invention experienced either stabilization or improvement of macular degeneration within one year of starting therapy. Of this percentage, approximately 65% of the patients subjected to the MCS therapy experienced improved vision, while approximately 32% experienced stabilization of macular degeneration (i.e., no further loss of vision).

U.S. Patent Publication 2008/0171929 by Katims published on Jul. 17, 2008 with the title "Method for standardizing spacing between electrodes, and medical tape electrodes," and is incorporated herein by reference. Patent Publication 2008/0171929 describes Standardization between paired electrodes is maintained in a medical device without needing a Mylar spreader, such as by forming the paired electrodes integrally with a tape part.

U.S. Pat. No. 4,018,218 to Carlson et al. issued on Apr. 19, 1977 with the title "Method and apparatus for sleep induction," and is incorporated herein by reference. U.S. Pat. No. 4,018,218 describes an apparatus and method to induce sleep in a patient that utilizes an oscillator to control the frequency of electric impulses received by the patient. First and second multivibrators generate the signals necessary to stimulate the central nervous system by conduction through the optic nerve tract, and also to generate a visual aura caused by stimulation of the retina of the eye. An amplifier amplifies the signals generated by the multivibrators and electrodes transmit the amplified signal to the patient. The various components of the apparatus may be stored in an eye frame structure wherein eye lid electrode pads are held in place contiguous the eyes of the patient, and wherein mastoid electrode pads are held in place by means of the frame ear hooks.

U.S. Pat. No. 5,522,864 to Wallace et al. issued on Jun. 4, 1996 with the title "Apparatus and method for ocular treatment," and is incorporated herein by reference. U.S. Pat. No. 5,522,864 describes that macular degeneration and other ocular pathology in a subject are treated by the steps of: placing a positive electrode of a direct current source in electrical contact with a closed eyelid of a subject; placing a negative electrode of the source in electrical contact with the posterior neck of the subject; and causing a constant direct current of 200 µA to flow between the electrodes through the subject for about 10 minutes. The source can be a portable, battery powered constant direct current generator which is affixed to the subject. The subject can ambulate during treatment.

U.S. Pat. No. 6,445,955 to Michelson et al. issued on Sep. 3, 2002 with the title "Miniature wireless transcutaneous electrical neuro or muscular-stimulation unit," and is incorporated herein by reference. U.S. Pat. No. 6,445,955 describes a miniature wireless transcutaneous electrical neuro or muscular stimulation unit. The unit has a housing attached to a plurality of electrodes. An electronics module containing an electrical circuit is contained within the housing and provides a sequence of monophasic or biphasic pulses to a patient's pain site via the electrodes. The electrodes can be disposable and come in a variety of shapes and sizes. The patient may select and control the intensity and the frequency of the pulses by choosing one of several TENS and microcurrent waveforms, as well as the orientation and quantity of the electrodes. The means for supplying power to the electronics module can be integrated with the electrodes in one detachable and disposable assembly. A worn-remote controller can send transmission signals to a receiver within the electronic module thereby allowing the patient to program specific units placed on the patient's body to perform operations in a specified series of waveforms. The electrodes may be embedded in a splint, bandage, brace or cast, where wires or flex-circuit material connect the electrodes to the unit. The electrodes can be arranged in a grid-like manner to allow for programming of a specific firing order which provides for greater therapeutic effect to a pain site, and may also be embedded in adhesive strips, similar to a conventional Band-Aid.

What is still needed is an improved method and apparatus for treating certain eye problems.

SUMMARY OF THE INVENTION

In some embodiments, the present invention provides an apparatus that includes: a disposable therapy appliance, wherein the disposable therapy appliance includes: a strip of material containing a plurality of electrodes configured to apply microcurrent stimulation therapy to a patient, wherein each electrode is no larger than 50 mm$^2$ (e.g., each electrode sized as a square about 7 mm by 7 mm, or a circle having a diameter of about 8 mm), and wherein the strip is shaped to be positioned to place electrodes on an upper eyelid and a lower eyelid of a patient's skin, and wherein each one of the plurality of electrodes is configured to be individually activated at a time for microcurrent stimulation without activation of any other ones of the plurality of electrodes during that time. In other embodiments, each electrode is no larger than 36 mm$^2$ (e.g., each electrode sized as a square no larger than about 6 mm by 6 mm, or a circle having a diameter of no larger than about 6.75 mm). In other embodiments, each electrode is no larger than 25 mm$^2$ (e.g., each electrode sized as a square no larger than about 5 mm by 5 mm, or a circle having a diameter of no larger than about 5.6 mm).

In some embodiments, the present invention applies microcurrent stimulation therapy to key points around the eye (and/or other body parts) for treatment of diseases such as macular degeneration, retinitis pigmentosa, glaucoma, optic neuritis, optic neuropathy, diabetic retinopathy, macular edema, papilledema, and other eye or nerve related, as well as other diseases, such as Bell's Palsy, requiring localized stimulation on other body parts.

In some embodiments of the apparatus, the strip of material includes an adhesive suitable to adhere the strip adhere to the skin.

In some embodiments of the apparatus, the strip of material includes an adhesive suitable to adhere the strip to a goggle device; and the apparatus further includes the goggle device, wherein the goggle device is shaped to hold the plurality of electrodes against the patient's skin without any adhesive touching the patient's skin. In some such embodiments, the apparatus further includes a vibrator connected to the goggle device to convey a gentle level of vibration as the microcurrent stimulation therapy is being applied.

In some embodiments, the present invention provides a method that includes: providing a disposable strip of material containing a plurality of electrodes configured to apply microcurrent stimulation therapy to a patient, wherein each electrode is no larger than 50 mm$^2$, and wherein the strip is shaped to be positioned to place electrodes on an upper eyelid and a lower eyelid of the patient's skin, wherein the electrodes are spaced at predetermined location points along the strip of material, and wherein each one of the plurality of electrodes is configured to be individually activated at a time for microcurrent stimulation without activation of any other ones of the plurality of electrodes during that time; providing a microcurrent-stimulation controller, wherein the electrodes are wired individually and separately to the microcurrent-stimulation controller; applying the disposable strip of material to the patient's skin; generating prescribed microcurrent pulses by the microcurrent-stimulation controller; and delivering the microcurrent pulses to each respective electrode of the plurality of electrodes in a temporal sequence.

BRIEF DESCRIPTION OF THE FIGURES

FIG. 1A is a schematic front-view diagram of a disposable eye-therapy appliance strip system 101 having four disposable curved linear adhesive therapy strips 115 positioned on the upper and lower eyelids of a person 99, showing exemplary positions of electrodes and connections to treatment apparatus, according to some embodiments of the present invention.

FIG. 1B is a front view of a system 102 showing an eye having two disposable adhesive therapy strips 115, one each positioned on the upper and lower eyelid of a person's eye 98, showing exemplary position of electrodes and connections to a micro-current stimulation controller apparatus 161, according to some embodiments of the present invention.

FIG. 1C is a side cross-section view a disposable adhesive therapy strip 115, according to some embodiments of the present invention.

FIG. 4A is a schematic back-side-view diagram of an eye-glass-frame 401 having two encircling strips 410, according to some embodiments of the present invention.

FIG. 4B is a schematic back-side-view diagram of an eye-goggle-frame 402 having two face-conforming encircling strips 412, according to some embodiments of the present invention.

FIG. 4C is a schematic top-side-view diagram of eye-goggle-frame 402 having two face-conforming encircling strips 412, according to some embodiments of the present invention.

FIG. 6A is a schematic front-view diagram of two single semi-encircling strip disposable therapy strips 615 forming a system 601, according to some embodiments of the present invention.

FIG. 6B is a plan-view diagram of a disposable set 660 of electrodes including a single semi-encircling strip disposable therapy strip 615 and a single "ground" electrode 641, according to some embodiments of the present invention.

DETAILED DESCRIPTION OF THE INVENTION

Figure 1D:
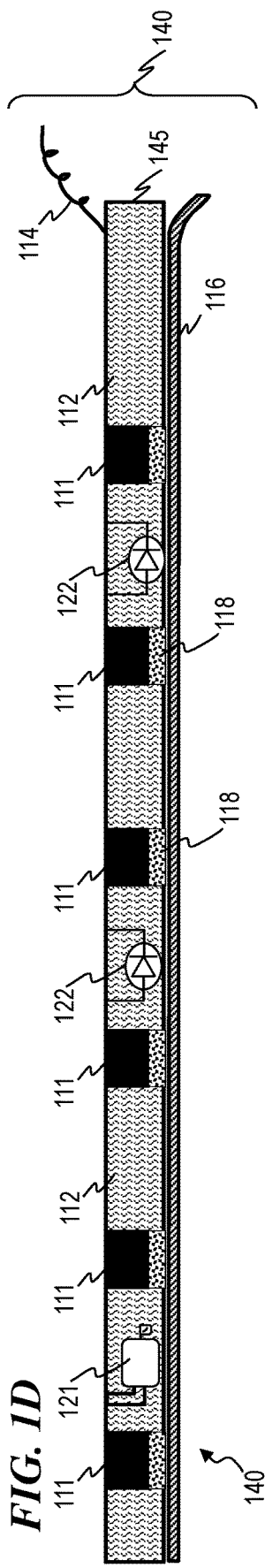
FIG. 1D is a schematic enlarged cross-section view a disposable adhesive therapy strip subsystem 140 including peel-away cover 116, according to some embodiments of the present invention.

Although the following detailed description contains many specifics for the purpose of illustration, a person of ordinary skill in the art will appreciate that many variations and alterations to the following details are within the scope of the invention. Specific examples are used to illustrate particular embodiments; however, the invention described in the claims is not intended to be limited to only these examples, but rather includes the full scope of the attached claims. Accordingly, the following preferred embodiments of the invention are set forth without any loss of generality to, and without imposing limitations upon the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

It is specifically contemplated that the present invention includes embodiments having combinations and sub-combinations of the various embodiments and features that are individually described herein (i.e., rather than listing every combinatorial of the elements, this specification includes descriptions of representative embodiments and contemplates embodiments that include some of the features from one embodiment combined with some of the features of another embodiment, including embodiments that include some of the features from one embodiment combined with some of the features of embodiments described in the patents and application publications incorporated by reference in the present application). Further, some embodiments include fewer than all the components described as part of any one of the embodiments described herein.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

Causes of AMD and Potential Treatment

Normal retinal cell function is a photochemical reaction converting light energy to an electrical impulse which travels to the brain and vision occurs. With AMD and other visual system diseases, diseased and inflamed retinal cells eventually lose cell function. Adenosine triphosphate (ATP) levels drop, protein synthesis drops, the electrical resistance goes up, and cell membrane electrical potential goes down limiting a cell's ability to move substrates into and out of a cell. The cells, without normal metabolic activity, go temporarily dormant for a time before prior to apoptosis.

It is believed that, when electrical stimulation is provided to the cells before they die, blood vessel permeability is increased, normal cellular electrical potential is reestablished or achieved, the ATP levels increase, protein synthesis will occur again, immature cell regeneration is activated, and normal cell metabolism is restored thereby improving or restoring vision function. In addition, in vitro studies have demonstrated that electrical stimulation appears to have a healing effect on the small blood vessels in the retina, promoting a more efficient delivery of nutrients to the retinal cells and a more efficient elimination of metabolic by-products.

The retinal pigment epithelium (RPE) is the support cell complex for the photosensitive rod and cone cells which make up the light-sensing structure of the retina. The RPE is the first to be affected by circulation impairment. Once affected by poor circulation, the RPE cannot efficiently assist the rods and cones in removing the metabolic and photo-chemical response by-products, which are essential for cellular function. Yellowish-colored sub-retinal deposits called "drusen" form when extracellular by-products are not carried away by blood circulating through the eye. As a result, the photoreceptor cells in the macula lose access to good blood flow and enter a dormant, toxic state and do not respond to light. If normal retinal cellular metabolism is not restored, the cells die and visual acuity is permanently lost. Thus, it is believed that micro-current stimulation will help rejuvenate the cells in the retina to slow or stop degeneration and in many cases trigger regeneration of retinal cells of the eye due to AMD.

While microcurrent stimulation therapy has been used to treat AMD and other visual system diseases, the methods and apparatus used in the prior art do not appear to maximize the therapeutic effect. Clinical studies have demonstrated that with the proper microcurrent stimulation waveform and therapy procedure, AMD may be slowed or stopped in a large number of people suffering from the disease, and in some patient groups vision can be restored. However, the efficacy of these therapies can be affected by the manual techniques medical professionals use to administer the therapy, or by the inefficient design and function of the medical device. When patients have significant skin impedance, or where there is a poor electrical conductivity, uptake of the stimulation level is limited and this may limit the treatment efficacy.

In some embodiments, the present invention includes a disposable adhesive therapy appliance that replaces the need for long manual applications of the microcurrent electro-stimulation therapy currently used or being envisioned as used by a clinical professional. Furthermore, the present invention also enables the clinician or physician to deliver stimulation to a particular designated point on the body, as opposed to a broader coverage or blanketed area of the body. Conventional technologies have two major drawbacks. First, when stimulation is delivered with a conventional probe or pointer, the probe or pointer is applied to the patient's skin manually and this takes a large amount of clinician time to administer the stimulation and properly deliver it. Secondly, when conventional gel strip or semi-circle or circles are used in any kind of electrostimulation or microcurrent therapy, the conventional gel strip or semi-circle or circles cover and deliver stimulation affecting a broad part of the human body, usually well in excess of 20 millimeters across. These conventional gel strips, semi-circles or circles do not permit the delivery of stimulation to a "pinpointed" area of two-to-fifteen (2-15) millimeters diameter. In contrast, the present invention allows for stimulation to a sequence of such "pinpointed" areas, and the present invention can, in certain treatment therapies, be more efficacious due to a greater stimulation level delivered on a smaller surface area, which penetrates more deeply and improves treatment performance.

FIG. 1A is a schematic front-view diagram of a disposable therapy-appliance strip system 101 having four disposable adhesive curved linear therapy strips 115 positioned on the upper and lower eyelids of the left and right eyes of a person 99, showing exemplary positions of electrodes 111 and connections to treatment-control apparatus 190, according to some embodiments of the present invention. In some embodiments, for each disposable adhesive curved linear therapy strips 115, each electrode 111 of a plurality of individually activatable electrodes 111 is coated with an electrically conductive gel and surrounded by an electrically insulating adhesive, in order that when an electrical signal is applied to a first selected electrode 111, the current goes into the tissue of the patient 99 only under that first electrode (and, in some embodiments, one or more other electrodes 111) when the signal from treatment-control apparatus 190 is active to the first electrode (and the one or more other electrodes 111 if those electrodes are also driven at that time). In some embodiments, the area of tissue under each one of a plurality of electrodes is between about 1 mm$^2$ and about 50 mm$^2$ (e.g., each electrode having electrical contact to skin in a square of about 1 mm by 1 mm to a square of about 7 mm by 7 mm, or a circle having a diameter of about 1.125 mm to about 8 mm). In some embodiments, each of a plurality of the electrodes 111 in disposable adhesive curved linear therapy strip 115 has a skin-contact area of about 1 mm$^2$ (e.g., a square of 1 mm by 1 mm or other suitable shape with that area). In some embodiments, each of a plurality of the electrodes 111 in disposable adhesive curved linear therapy strip 115 has a skin-contact area of about 0.75 mm$^2$ (e.g., a square of 0.866 mm by 0.866 mm, or a circle having a diameter of about 1 mm, or other suitable shape with that area). Some other embodiments include a plurality of the electrodes 111 in disposable adhesive curved linear therapy strip 115 wherein each electrode has a skin-contact area of between about 1 mm$^2$ and about 4 mm$^2$, a plurality of the electrodes 111 in disposable adhesive curved linear therapy strip 115 wherein each electrode has a skin-contact area of about 4 mm$^2$, a plurality of the electrodes 111 in disposable adhesive curved linear therapy strip 115 wherein each electrode has a skin-contact area of between about 4 mm$^2$ and about 9 mm$^2$, a plurality of the electrodes 111 in disposable adhesive curved linear therapy strip 115 wherein each electrode has a skin-contact area of about 9 mm$^2$, a plurality of the electrodes 111 in disposable adhesive curved linear therapy strip 115 wherein each electrode has a skin-contact area of between about 9 mm$^2$ and about 16 mm$^2$, a plurality of the electrodes 111 in disposable adhesive curved linear therapy strip 115 wherein each electrode has a skin-contact area of about 16 mm$^2$, and/or a plurality of the electrodes 111 in disposable adhesive curved linear therapy strip 115 wherein each electrode has a skin-contact area of between about 16 mm$^2$ and about 25 mm$^2$ (e.g., a square of 5 mm by 5 mm or other suitable shape with that area). In some other embodiments, each of a plurality of the electrodes 111 in disposable adhesive curved linear therapy strip 115 is substantially circular with a diameter of about 1 mm (a skin-contact area of about 0.8 mm$^2$), while some other embodiments include a plurality of substantially circular electrodes 111 each having a diameter of about 1.28 mm (a skin-contact area of about 1 mm$^2$), a plurality of substantially circular electrodes 111 each having a diameter of about 2 mm (a skin-contact area of about 3 mm$^2$), a plurality of substantially circular electrodes 111 each having a diameter of about 3 mm (a skin-contact area of about 7 mm$^2$), a plurality of substantially circular electrodes 111 each having a diameter of about 4 mm (a skin-contact area of about 13 mm$^2$), a plurality of substantially circular electrodes 111 each having a diameter of about 5 mm (a skin-contact area of about 20 mm$^2$), and/or a plurality of substantially circular electrodes 111 each having a diameter of about 6 mm (a skin-contact area of about 28 mm$^2$). In some embodiments, each electrode is no larger than 50 mm$^2$ (e.g., each electrode sized as a square about 7 mm by 7 mm, or a circle having a diameter of about 8 mm) and wherein the strip is shaped to be positioned to place electrodes on an upper eyelid and a lower eyelid of a the patient's skin, and wherein each one of the plurality of electrodes is configured to be individually activated at a time for microcurrent stimulation without activation of any other ones of the plurality of electrodes during that time. In some embodiments, each electrode is between about 36 mm$^2$ and about 50 mm$^2$. In other embodiments, each electrode is no larger than 36 mm$^2$ (e.g., each electrode sized as a square no larger than about 6 mm by 6 mm, or a circle having a diameter of no larger than about 6.75 mm). In some embodiments, each electrode is between about 25 mm$^2$ and about 36 mm$^2$. In other embodiments, each electrode is no larger than 25 mm$^2$ (e.g., each electrode sized as a square no larger than about 5 mm by 5 mm, or a circle having a diameter of no larger than about 5.6 mm).

In some embodiments, each disposable therapy-appliance strip 115 includes electrical conductors 114 electrically coupled to treatment-control apparatus 190. In some embodiments, treatment-control apparatus 190 is located locally (e.g., in a battery operated unit that is carried by person 99, such as in a shirt pocket or head-mounted elastic band), while in other embodiments, treatment-control apparatus 190 is attached to or part of a computer-controlled apparatus such as a laptop personal computer, a tablet computer, a desktop computer or the like. Therapy signals from the signal source 190 are carried by the connection wire bundle 114 to electrodes 111, which deliver the current load to the patient's tissue.

FIG. 1B is a front view of a system 102 showing one eye having two disposable therapy-appliance strips 115, one each positioned on the upper and lower eyelid of a person's eye 98, showing exemplary position of electrodes and connections to a micro-current stimulation controller apparatus 161, according to some embodiments of the present invention. In some embodiments, micro-current stimulation controller apparatus 161 includes a microprocessor (µP) operated by a battery, and optionally is controlled and/or programmed by a nearby laptop personal computer, a tablet computer, a desktop computer or the like. In some embodiments, each disposable therapy-appliance strip 115 includes electrical conductors 114 electrically coupled to an electrical connector 117 that plugs into or otherwise electrically connects to a corresponding connector 162 on controller apparatus 161.

FIG. 1C is a side cross-section view of a disposable therapy-appliance strip 115, according to some embodiments of the present invention. As noted above, in some embodiments, each one of a plurality of individually activatable electrodes 111 is coated with an electrically conductive gel and surrounded by an electrically insulating adhesive, in order that when an electrical signal is applied only to a first selected electrode 111, the current goes into the tissue of the patient 99 only under that first electrode. In some embodiments, only one selected electrode 111 is activated (driven by a pulsed electrical signal) at any one time, and each of a plurality of the electrodes 111 is sequentially driven by temporally separated pulses. In some embodiments, two or more of a plurality of the electrodes 111 are driven by simultaneous pulses or by pulses that at least partially overlap in time. In some embodiments, each one or a plurality of subsets of the electrodes is tested to determine which are most effective at relieving symptoms and/or which, when driven by pulsed signals, may cause a worsening of symptoms. Based on the empirical results of such testing of subsets of the electrodes, the system (e.g., system 102 of FIG. 1B) selectively activates those set(s) of electrodes 111 and the sequences of pulses that have been determined empirically to be effective and avoids activation of those set(s) of electrodes 111 and the sequences of pulses that have been determined empirically to worsen symptoms. The connection wire bundle (e.g., a cable having a plurality of electrical conductors) 114 is shown leading to the strip substrate 112 containing the electrodes 111.

FIG. 1D is a schematic enlarged cross-section view of a disposable therapy-appliance strip subsystem 140 including therapy-appliance strip 145 and peel-away cover 116, according to some embodiments of the present invention. In some embodiments, disposable therapy-appliance strip 145 includes electrodes 111 that are equivalent to those in disposable therapy-appliance strip 115 described above, however, disposable therapy-appliance strip subsystem 140 further includes one or more light emitting features 122 (such as light-emitting diodes (LEDs) mounted in or on disposable therapy-appliance strip 145, or light-conducting optical fibers connected to LEDs in micro-current stimulation controller apparatus 161 or treatment-control apparatus 190 described above) and/or one or more vibration units 121. In some embodiments, light emitting features 122 are activated to emit light pulses at the same time that electrical treatment signals are applied to one or more electrodes 111 to provide feedback to patient 99 and/or to the medical care professional who is monitoring the procedure, in order to provide to them feedback to indicate that the procedure is in process. In some embodiments, vibration units 121 are activated to gently vibrate the eyelids of patient 99 at the same time that electrical treatment signals are applied to one or more electrodes 111 to provide feedback to patient 99, in order to provide to them feedback to indicate that the procedure is in process. In some embodiments, therapy-appliance strip subsystem 140 includes the optional addition of one or more motors 121 and/or one or more LEDs 122 for feedback. In some embodiments, the LED(s) provide a visually perceivable indication of the functioning operation of therapy strip 145 as feedback to patient 99 and/or to the medical professional supervising the treatment that the device is functioning and/or an indication of which therapy protocol (e.g., one of a plurality of selectable protocols) is being applied and/or an indication of how much time is remaining in the present session (or how much time has elapsed since the start of the present session). In some embodiments, the one or more motors 121 drive an off-balance shaft that provides a tactile vibration to the patient's eyelid). In some embodiments, the light emitter(s) 122 on the strip indicates, via a single light or multiple lights, what the apparatus status is: off, in-treatment, intermittent connections, inappropriate electrical impedance, and/or insufficient stimulation, and/or progress status of therapy (e.g., whether the session is ¼, ½, ¾, or ⅞ finished). In some embodiments, the light from LED(s) 122 is made to be visible through the patient's closed eyes to indicate that the therapy session is "in treatment and working," or whether the session is finished. In some embodiments, the light emission from LED(s) 122 is also visible externally so that the clinician can assess the status of the treatment therapy in session on a patient-by-patient basis without referring to a display screen on base station 790. In some embodiments, the application of an amount of microcurrent into one of the electrodes (e.g., in some embodiments, about 200 microamps or more may cause some patients to perceive a microcurrent-caused flash of light and/or a sensation of vibration) from the microcurrent applied into and around the eye, even in the absence of LED light emission from LEDs 122, and thus the emission of light from the LED(s) 122, and/or the vibration from motors 121, can be used to mask from the patient whether or not microcurrent pulses were applied through one of the electrodes 111. For the purposes of testing the efficacy (wherein efficacy can be defined as the performance of a therapy under ideal and controlled circumstances) and/or effectiveness (wherein effectiveness refers to the therapy's performance under "real-world" conditions) of the pulsed microcurrent therapy of the present invention, it can be useful to supply a subset of patients with actual therapy along with light from the LED(s) 122, and/or vibration from motors 121 while presenting a different subset of patients with sham or placebo therapy with the difference (between the actual and sham sessions) masked, from the patient as well as from the medical professional supervising the treatment by light from the LED(s) 122, and/or vibration from motors 121 (i.e., using double-blind experiments). In some embodiments, the conductive gel 118 on each electrode 111 is kept moist and separated from the gel 118 on other electrodes 111 by cover 116 until therapy-appliance strip 140 is prepared for use by removing cover 116, thus exposing the gel 118.

Figure 1E:
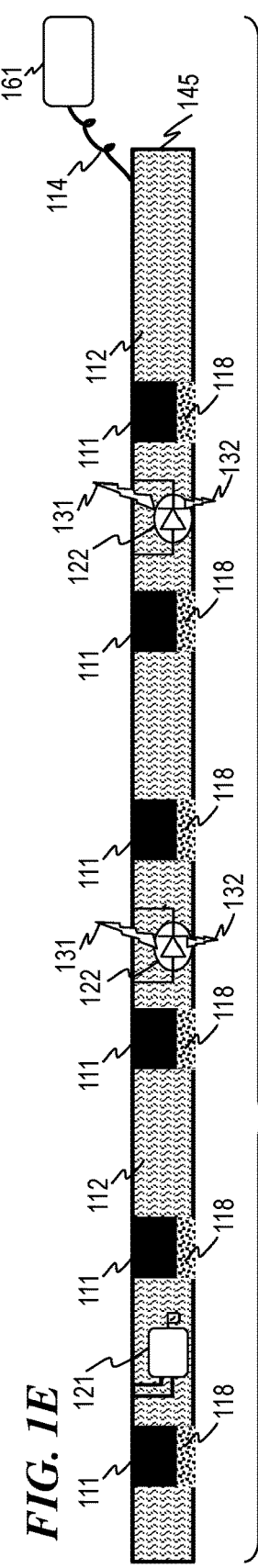
FIG. 1E is a schematic enlarged cross-section view a disposable adhesive therapy strip 145 without peel-away cover 116, according to some embodiments of the present invention.

FIG. 1E is a schematic enlarged cross-section view of a disposable therapy strip 145, (i.e., disposable therapy-appliance strip subsystem 140 with the peel-away cover 116 having been removed) connected to a micro-current stimulation controller apparatus 161 to form therapy system 146, according to some embodiments of the present invention. This therapy system 146, in contrast to just therapy-appliance strip 145 of therapy-appliance strip subsystem 140, includes the addition of the micro-current stimulation controller apparatus 161 connected by signal cable 114, wherein controller 161 drives the light signal 131, which goes toward the operator, and light signal 132, which goes toward the patient 99 (e.g., in some embodiments, through the patient's eyelid).

Figure 1F:
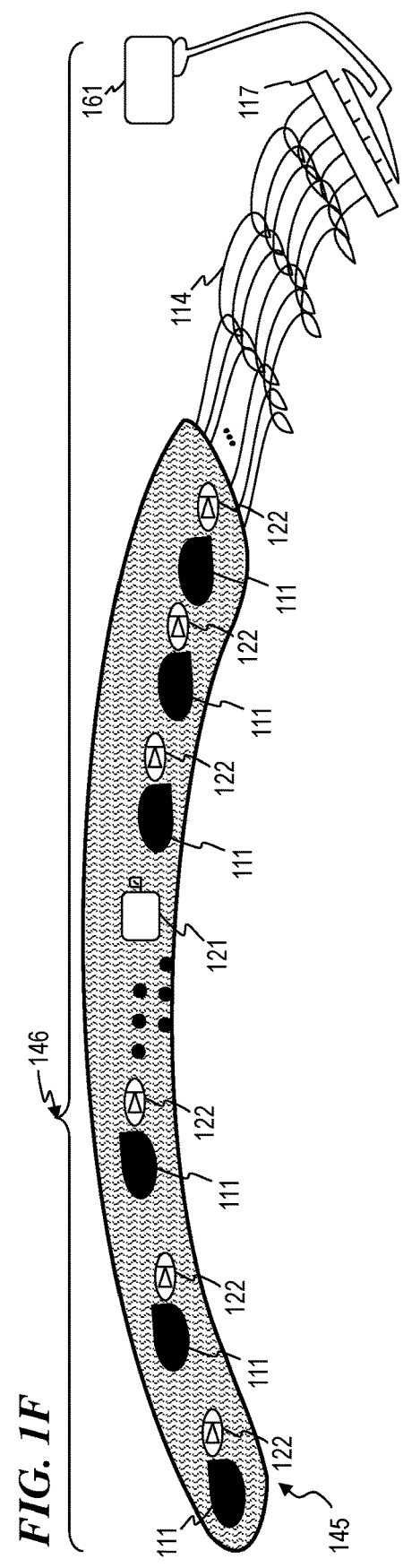
FIG. 1F is a schematic enlarged front view a disposable adhesive therapy strip subsystem 140, according to some embodiments of the present invention.

FIG. 1F is a schematic enlarged front view of a disposable therapy system 146, according to some embodiments of the present invention. As noted above, one or more light emitting features 122 and/or one or more vibration units 121 are provided in each disposable therapy-appliance strip 145. In some embodiments, one LED 122 is provided for each electrode 111 and each LED 122 is activated at the same time as the corresponding electrode 111. In some embodiments, each LED 122 is located adjacent to, or directly above or below, the corresponding electrode 111. This view of the device 140 also shows the connector 117 for the wire bundle 114.

Figure 1G:
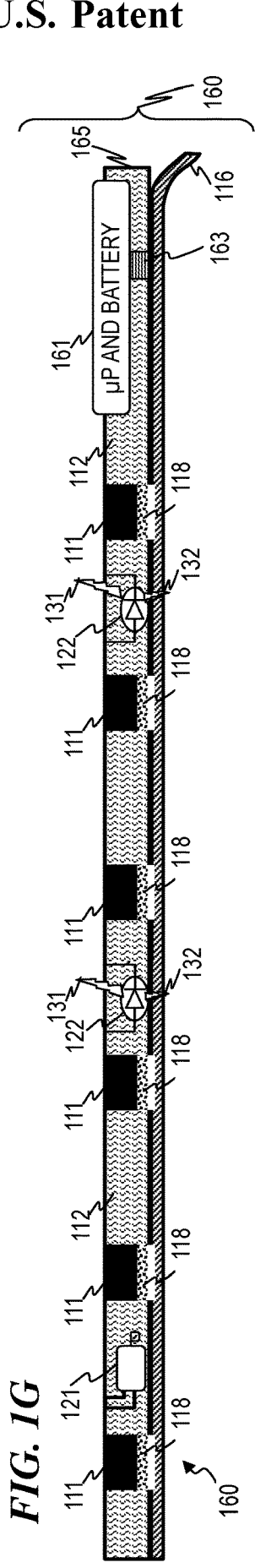
FIG. 1G is a schematic enlarged cross-section view a disposable adhesive therapy strip subsystem 160, according to some embodiments of the present invention.

FIG. 1G is a schematic enlarged cross-section view of a disposable therapy-appliance strip subsystem 160 including therapy-appliance strip 165 and, according to some embodiments of the present invention. In some embodiments, disposable therapy-appliance strip subsystem 160 is a single-use product that includes a built-in microprocessor-and-battery unit 161 in the disposable therapy-appliance strip subsystem 160. In some embodiments, the battery in unit 161 is air-activated via vent 163 and removal of the protective air-barrier peel-away cover 116 activates the battery by letting air into vent 163. In some embodiments, an auxiliary disposable therapy-appliance strip 145 (i.e., a strip without the built-in microprocessor-and-battery unit 161 that is applied to one eyelid) can be connected to an activated disposable therapy-appliance strip 160 attached to the other eyelid such that the single microprocessor-and-battery unit 161 controls operation (sends treatment signals to, and receives feedback signals from, the electrodes 111, LEDs 122, and/or vibration units 121) in both disposable therapy-appliance strip 165 and the connected disposable therapy-appliance strip 145. In some embodiments, the micro-current stimulation controller apparatus 161 is attached to (and is part of) the strip 112, with an air vent 163 that passes through substrate 112 to allow air to contact and activate the battery in controller apparatus 161. In some embodiments, controller apparatus 161 is actively controlled wirelessly, during operation (e.g., using protocol and circuitry such as Bluetooth®, near-field communications (NFC), or the like) from a nearby computer (such as a tablet, desktop or laptop), while in other embodiments, controller apparatus 161 is similarly wirelessly programmed before operation, and thereafter operates autonomously based on the program. In some such embodiments, controller apparatus 161 transmits, back to the nearby computer, sensed signals that are then used to determine therapy efficaciousness and/or to control the therapy stimulation signals. In some embodiments, the sensed signals transmitted to the nearby computer include sensed electrical impedance measurements for safety monitoring and control, and/or sensed nerve electrical signals, sensed from the patient's skin, that might indicate patient discomfort or pain and that are then used to limit the stimulation signals that would cause such a reaction in the patient. In some embodiments, one or more of the electrodes 111 that are not at the time being used to deliver therapy stimulation signals are instead used to sense nerve electrical signals from the patient's eyelid, and to deliver the sensed signals to an attached controller apparatus.

Figure 2C:
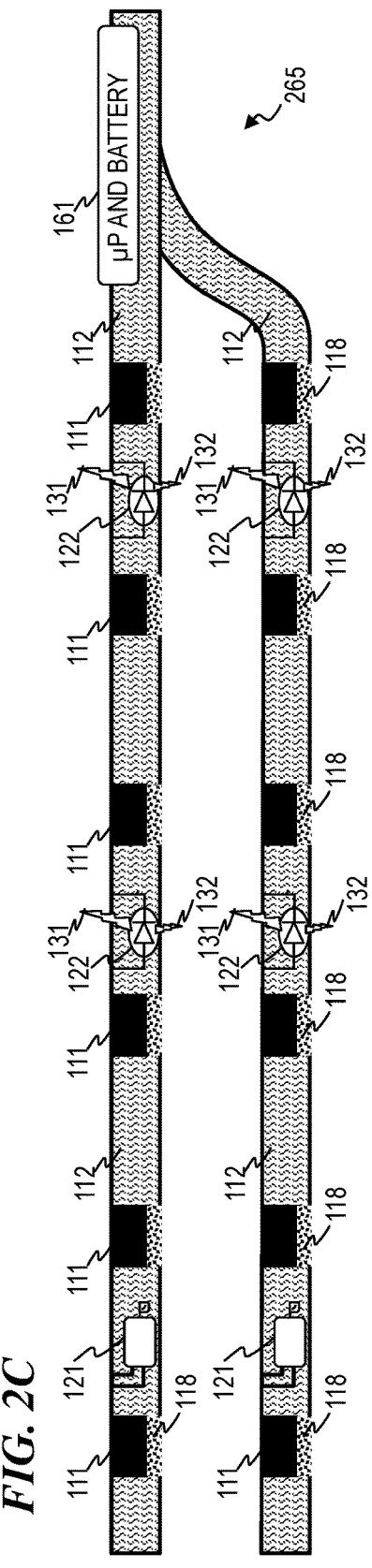
FIG. 2C is a side cross-section view of a disposable partially encircling therapy-appliance strip 265, according to some embodiments of the present invention.
Figure 3C:
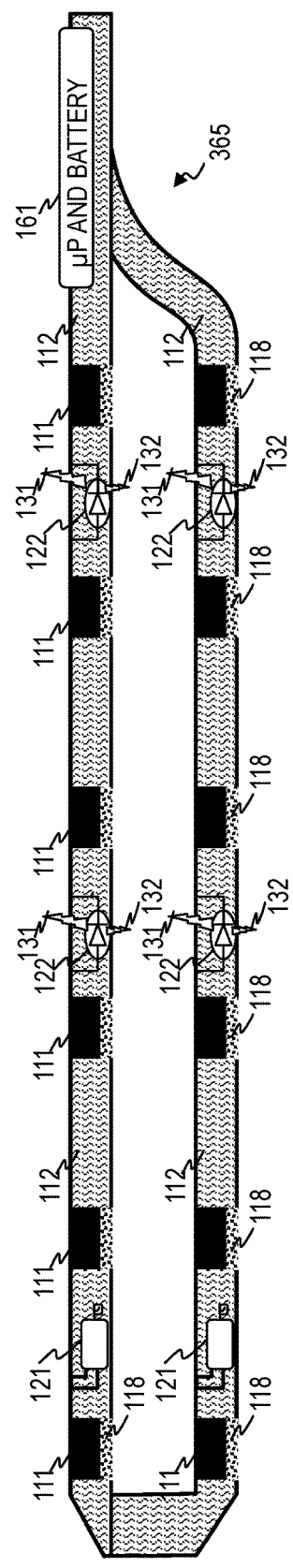
FIG. 3C is a side cross-section view a disposable therapy strip 365, according to some embodiments of the present invention.

FIG. 2C and FIG. 3C are described below.

Figure 2B:
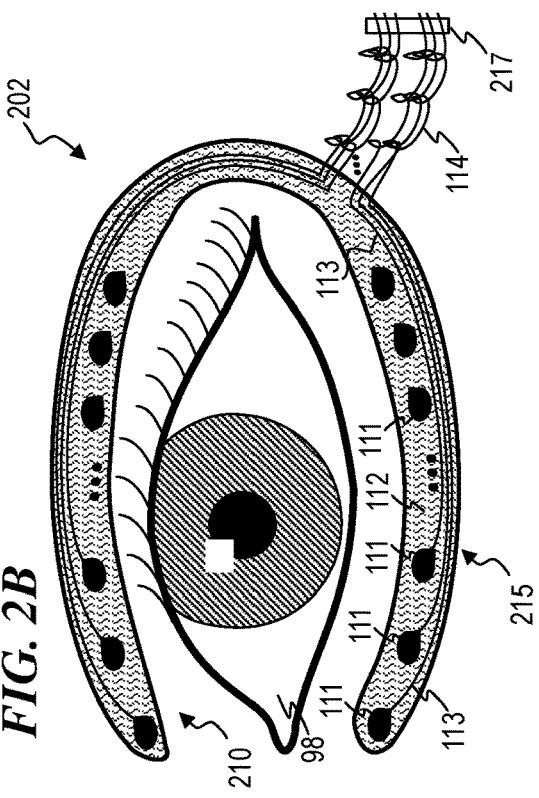
FIG. 2B is an enhanced detail view of a system 202 on the upper and lower eyelid around a patient's eye 98 of disposable partially encircling eye therapy-appliance strip 215 positioned on the upper and lower eye lid showing position of electrodes and connections to micro-current stimulation controller apparatus, according to some embodiments of the present invention.
Figure 2A:
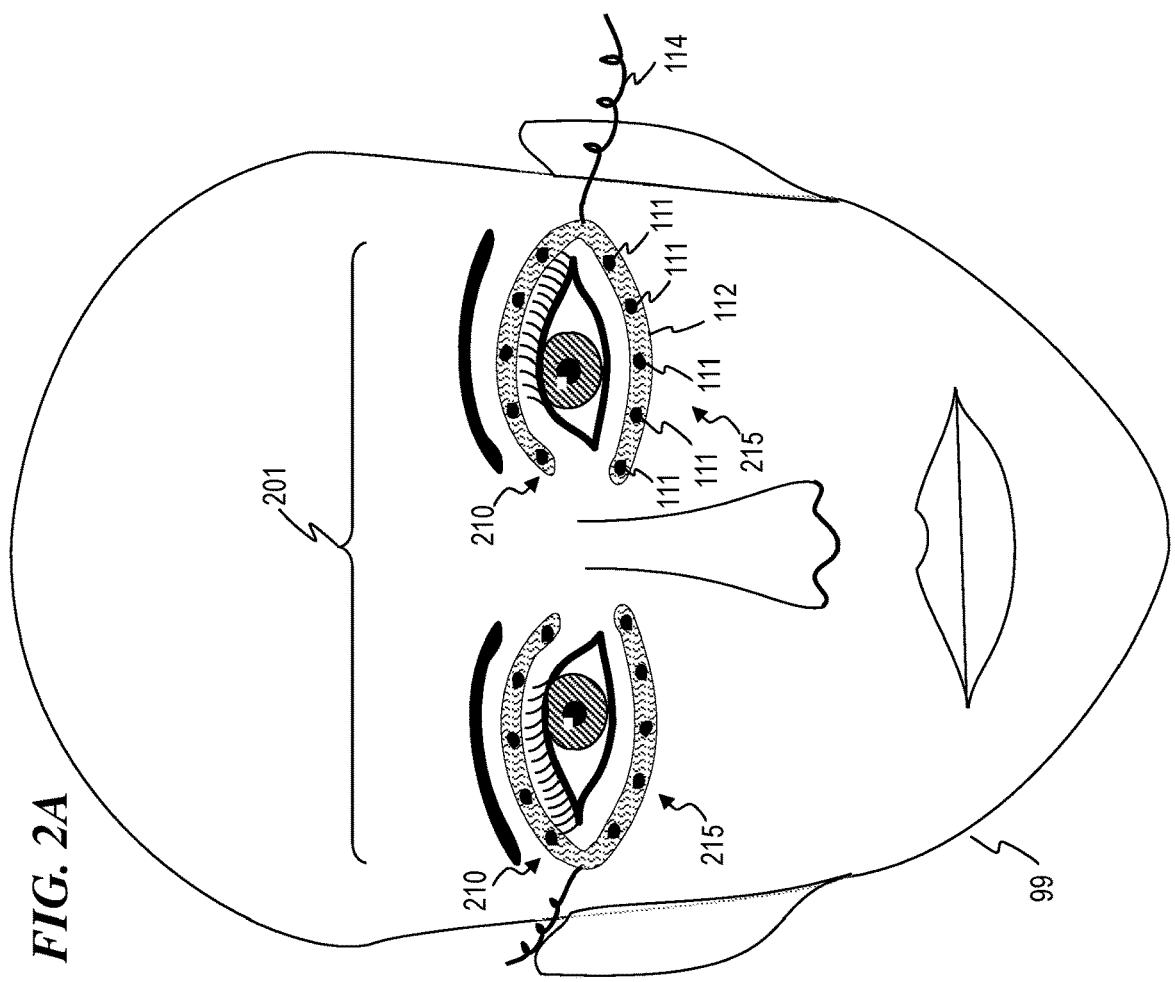
FIG. 2A is a schematic front-view diagram of a disposable partially encircling eye-therapy appliance strip system 201, using two single adhesive therapy strips 215 with electrodes for both upper and lower eye lid showing position of electrodes and cable to micro-current stimulation controller apparatus, according to some embodiments of the present invention.

FIG. 2A is a schematic front-view diagram of a disposable appliance partially encircling eye strip system 201, using, on each eye, a single partially encircling eye strip 215 with electrodes for both upper and lower eye lid showing position of electrodes 111 and cable 114 to a micro-current stimulation controller apparatus (not shown here—see FIG. 1A for an example), according to some embodiments of the present invention. In some embodiments, a single partially encircling eye strip 215 is functionally the same as a pair of curved linear therapy strip 115 as described for FIG. 1A, however single partially encircling eye strip 215 provides the advantage that the upper-lid portion and the lower-lid portion are automatically aligned relative to one another, and the connections to the current stimulation controller apparatus is simpler. The various reference numbers in FIG. 2A are as described above for FIG. 1A.

FIG. 2B is an enhanced detail view on eye of disposable appliance partially encircling eye strip 215 positioned on the upper and lower eyelid showing position of electrodes and connections to micro-current stimulation controller apparatus, according to some embodiments of the present invention. In some embodiments, the single connector 217 shown here replaces the two connectors 117 of FIG. 1B. The other various reference numbers in FIG. 2B are as described above for FIG. 1B.

FIG. 2C is a side cross-section view of a disposable partially encircling therapy-appliance strip 265, according to some embodiments of the present invention, including a micro-current stimulation controller apparatus 161 on the strip 265. The other various reference numbers in FIG. 2C are as described above for FIG. 1G.

Figure 3B:
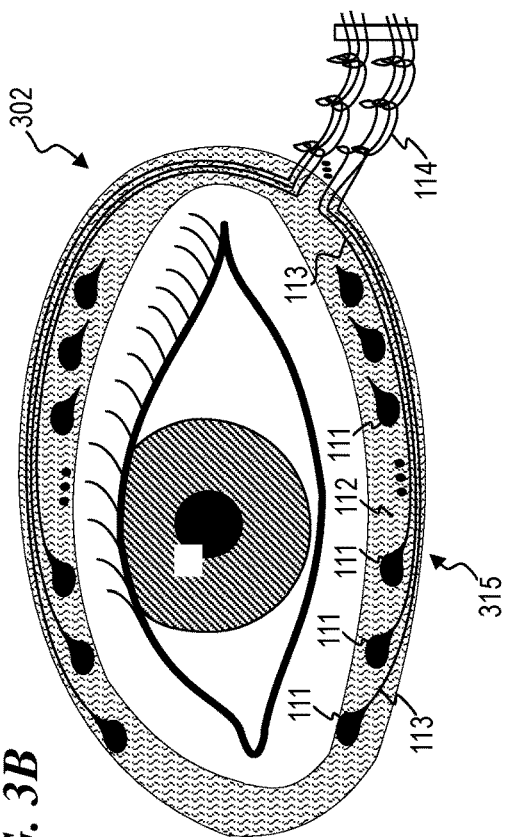
FIG. 3B is an enhanced detail view of a system 302 on the upper and lower eyelid around a patient's eye 98 of disposable eye-encircling therapy strip 310 positioned on the upper and lower eye lid showing position of electrodes and connections to micro-current stimulation controller apparatus, according to some embodiments of the present invention.
Figure 3A:
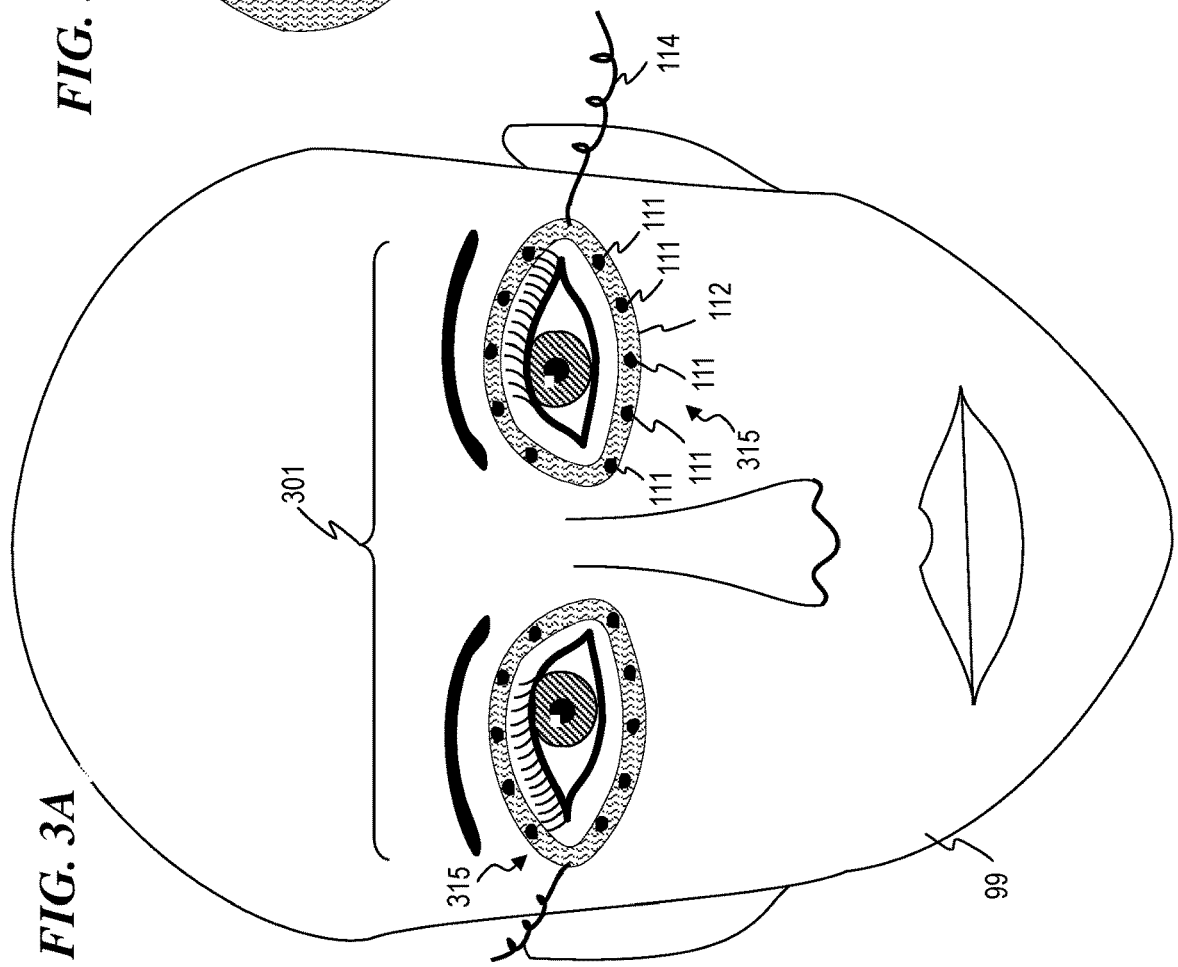
FIG. 3A is a schematic front-view diagram of two single encircling strip disposable therapy strips 310 forming a system 301, according to some embodiments of the present invention.

FIG. 3A is a schematic front-view diagram of two single encircling strip disposable therapy strips 315 forming a system 301, according to some embodiments of the present invention. In some embodiments, each of the disposable therapy strips 315 is functionally the same as a pair of curved linear therapy strip 115 as described for FIG. 1A, or a single partially encircling eye strip 215, but each of the disposable therapy strips 315 provides the advantage that the upper-lid portion and the lower-lid portion are automatically aligned relative to one another at both ends. The various reference numbers in FIG. 3A are as described above for FIG. 2A.

FIG. 3B is an enhanced detail view on eye of disposable eye-encircling therapy strip 315 positioned on the upper and lower eye lid showing position of electrodes and connections to micro-current stimulation controller apparatus, according to some embodiments of the present invention. In some embodiments, the single connector 317 shown here replaces the two connectors 117 of FIG. 1B. The other various reference numbers in FIG. 3B are as described above for FIG. 1B.

FIG. 3C is a side cross-section view of a disposable therapy strip 365, according to some embodiments of the present invention, including a micro-current stimulation controller apparatus 161 included on the strip 365. The other various reference numbers in FIG. 3C are as described above for FIG. 1G.

FIG. 4A is a schematic back-side-view diagram of an electrode-containing eye-glass-frame 401 having two encircling frame members 410 each having a plurality of electrodes 111 positioned on strips on the periphery of each frame member 410, according to some embodiments of the present invention. In some embodiments, eye-glass-frame 401 includes mechanical connectors 421 and 422 on the temple tips of elastic side members 420 that provide an adjustable-length holding mechanism to snugly hold frame members 410 against the orbital bone and/or eyelids of the patient, and a stretchy (elastic) bridge 414 that provides an adjustable inter-ocular distance between the left and right eye of the patient. In some embodiments, each one of a plurality of conductors in cable 114 is electrically connected to a corresponding one of the plurality of electrodes 111. In some embodiments, each encircling frame member 410 differs from the single encircling strip disposable therapy strips 315 in that no adhesive is used to hold the electrodes against the eyelids of the patient; rather, the elastic side members 420 wrap around the head of the patient to snugly hold the electrodes 111 against the skin of the patient around the patient's eyes. The absence of adhesive is an advantage in removing the electrodes from the patient as compared to, for example, removing two single encircling strip disposable therapy strips 315 of a system 301. The absence of adhesive is also an advantage for patients who may be allergic or sensitive to the adhesive. The other various reference numbers in FIG. 4A are as described above for FIG. 3A.

FIG. 4B is a schematic back-side-view diagram of an electrode-containing eye-goggle-frame 402 having two face-conforming eye-encircling strips 412, according to some embodiments of the present invention.

FIG. 4C is a schematic top-side-view diagram of eye-goggle-frame 402 having two face-conforming encircling strips 410, according to some embodiments of the present invention. In some embodiments, eye-goggle-frame 402 includes a stiff two-part frame member 433 having an elastic bridge connector 414 flexibly and stretchily holding the two parts to one another while providing the stretch capability to vary the distance between to match the eyes of the patient. In some embodiments, each face-conforming eye-encircling strip 412 is positioned on a flexible compressible elastic extension 431 that extends backward (toward the patient's face) from a corresponding base 432 that is attached to the two-part frame member 433. The flexible compressible elastic extension 431 allows each eye-encircling strip 412 to better conform to the patient's face. In some embodiments, a cable 114 (connecting to, or extending as, electrical wiring within electrode-containing eye-goggle-frame 402 to connect to the electrodes 111) extends from one side or both sides of two-part frame member 433, and conducts electrical stimulation and/or sensing signals between an external controller (not shown here) and the electrodes 111. In some embodiments, each eye-encircling strip 412 is more flexible than encircling frame member 410, and again differs from the single encircling strip disposable therapy strips 315 in that no adhesive is used to hold the electrodes against the eyelids of the patient; rather, the elastic side members 420 wrap around the head of the patient to snugly hold the electrodes 111 against the skin of the patient around the patient's eyes. The other various reference numbers in FIGS. 4B and 4C are as described above for FIG. 4A.

Figures 5A, 5B:
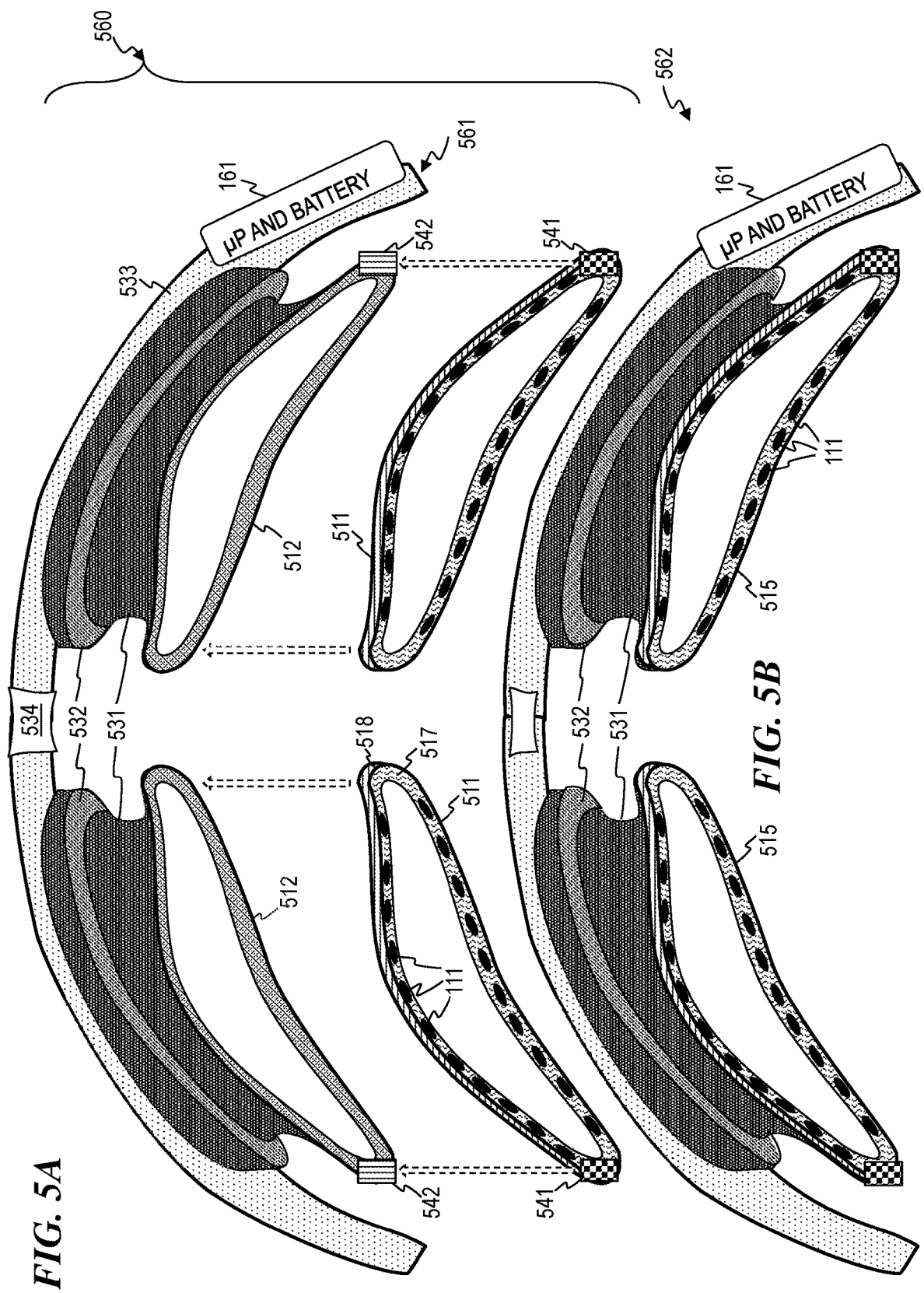
FIG. 5A is a schematic exploded top-side-view diagram 560 of an eye-goggle-frame 560 having two yet-to-be-attached disposable adhesive eye encircling strips 511, according to some embodiments of the present invention.
FIG. 5B is a schematic assembled top-side-view diagram of eye-goggle-frame 561 having two attached disposable adhesive eye encircling strips 515, according to some embodiments of the present invention.

FIG. 5A is a schematic exploded top-side-view diagram of an eye-goggle-frame 560 having two yet-to-be-attached disposable adhesive eye-encircling strips 511, according to some embodiments of the present invention. In some embodiments, the adhesive on the removable and replaceable eye-encircling strips 511 is on the frame side (not on the side that touches the patient's face) and adheres eye-encircling strips 511 to surface 512 on the elastic cups 531. In some embodiments, electrical connectors 541 on the strips 511 electrically connect to matching cup-side connectors 542 on surface 512 of the flexible compressible elastic extension 531. As with the device of FIGS. 4B and 4C, in some embodiments, eye-goggle-frame 561 includes a stiff two-part frame member 533 having an elastic bridge connector 534 flexibly and stretchily holding the two parts of frame member 533 to one another while providing the stretch capability to vary the eye-to-eye distance between the two parts to match the eyes of the patient. In other embodiments, frame 533 is a single stiff piece (omitting elastic bridge connector 534) and the flexible compressible elastic extensions 531 provide the lateral eye-to-eye distance compensation. In some embodiments, each face-conforming eye-encircling strip-receiving surface 512 is positioned on a flexible compressible elastic extension 531 that extends backward (toward the patient's face) from a corresponding base 532 that is attached to the frame member 533. The flexible compressible elastic extension 531 allows each eye-encircling strip 511 (which is adhered to flexible surface 512) to better conform to the patient's face. In some embodiments, each eye-encircling strip 511 includes a double-sided pressure-sensitive-adhesive-coated foam layer 518, adhered on one of its faces to a hypo-allergenic substrate 517 on which are deposited a plurality of electrodes 111 each individually electrically connected by a conductor (also deposited on substrate 517) to a separate corresponding contact on electrical connector 541. In some embodiments, a first peel-away protective layer on the frame side of double-sided pressure-sensitive-adhesive-coated foam layer 518 is removed so that eye-encircling strip 511 can be stuck (adhered) to strip-receiving surface 512. In some embodiments, a small glob of electrically conductive gel is deposited on each electrode 111, and a second peel-away adhesive-coated protective layer is provided on the patient-skin side of eye-encircling strip 511 that covers electrodes 111 and the gel, wherein the second peel-away protective layer keeps each glob of gel on its corresponding electrode 111 and separated from neighboring electrodes until the second peel-away protective layer is removed immediately prior to use. In some embodiments, a vibration motor such as vibrator 121 of FIG. 1D is incorporated in disposable strip 511. In some embodiments, one or more LEDs 122 (such as those of FIG. 1D) are incorporated in disposable strip 511. In some embodiments, a vibration motor such as vibrator 121 of FIG. 1D is instead incorporated in eye-goggle-frame 560 rather than being part of the disposable strip 511. In some embodiments, one or more LEDs 122 (such as those of FIG. 1D) are instead incorporated in eye-goggle-frame 560 rather than being part of the disposable strip 511.

In some embodiments, a controller 161 (e.g., a microprocessor (optionally including an RF (radio-frequency) transceiver that communicates with a remote PC (personal computer), tablet, laptop or the like) and battery) is mounted to, or is built-in and part of, one side or both sides of two-part frame member 533, and conducts electrical stimulation and/or sensing signals between an external controller (not shown here) and the electrodes 111. In some embodiments, each eye-encircling strip 511 and its mounting surface 512 is more flexible than encircling frame member 410 of FIG. 4A, and again differs from the single encircling strip disposable therapy strips 315 in that no adhesive is used to hold the electrodes against the eyelids of the patient; rather, in some embodiments, an elastic band (not shown here, but similar to band 662 of FIG. 6A) wraps around the head of the patient to snugly hold the electrodes 111 against the skin of the patient around the patient's eyes (e.g., on the upper and lower eyelids, and/or on the supraorbital bone (the supraorbital foramen of the frontal bone of the skull) and/or infraorbital bone (the front of the zygomatic bone and/or maxilla)).

FIG. 5B is a schematic assembled top-side-view diagram of an assembled eye-goggle-frame 562 having two disposable adhesive eye encircling strips 515, according to some embodiments of the present invention. In some embodiments, the two disposable adhesive eye encircling strips 515 are removably adhered to the mounting surfaces 512 of eye-goggle-frame 561 and the electrical contacts 541 and 542 are connected to one another. Note that reference number 515 refers to each eye-encircling strip 511 after it is adhered to and electrically connected to eye-goggle-frame 561, and reference number 562 refers to the combination of eye-goggle-frame 561 after the two eye-encircling strips 511 are adhered to and electrically connected to eye-goggle-frame 561. In some embodiments, a small amount of electrically conductive gel is deposited on each electrode 111. In some embodiments, a through-hole opening all the way through eye-goggle-frame 561 is left in front of each of the patient's eyes (wherein one of the adhesive eye encircling strips 515 surrounds each of these through-hole openings) such that the patient can see the surrounding environment during the therapy session, in order to reduce claustrophobia, fear or other stress conditions for the patient. In other embodiments, a translucent or opaque covering is provided in order the encourage the patient to minimize eye movement so that the sequence of therapy stimulation pulses continue to stimulate the desired tissue volumes throughout the therapy session. In some embodiments, one or both of adhesive eye encircling strips 515 further include one or more LEDs (such as, for example, LEDs 122 of FIG. 1D) that provide the optical indicator function described above, and/or one or more vibration units (such as, for example, vibration units 121 of FIG. 1D) that provide the tactile-feedback function described above. The other various reference numbers in FIGS. 5A and 5B are as described above for FIG. 4A.

FIG. 6A is a schematic front-view diagram of a system 601 that includes two single semi-encircling disposable therapy strips 615 that together with controller 661 and its elastic head strap 662 forming a system 601, according to some embodiments of the present invention. In some embodiments, system 601 includes one or more electrodes 641, which are placed in contact with skin on the neck of patient 99, and attached to the main device (controller 661) by conductor (e.g., in some embodiments, wire) 642. In some embodiments, a nose-pad and pad-arm unit 651 is provided to support the controller 661 on the forehead of patient 99 over the patient's eyes 98. In some embodiments, the therapeutic electrical-stimulation pulses are applied in a sequence (one at a time) to the electrodes 111 on therapy strips 615 surrounding each eye, wherein the return path (i.e., the ground signal) is provided through electrodes 641 (in some embodiments, one or more electrodes 641 is adhesively a coupled to the neck of patient 99; e.g., one to each side of the neck as shown). In some embodiments, uniphasic signals are applied to the eye electrodes (either all positive voltages relative to ground electrode(s) 614, or all negative relative to ground electrode(s) 614) in order to accumulate the desired ionic molecules in or near the retinas of the patient). In other embodiments, balanced biphasic signals are applied to the eye electrodes (alternating with some positive voltages and some negative voltages relative to ground electrode(s) 614, or by applying differential signals to selected pairs of electrodes 111 without using a ground signal to ground electrode(s) 614, and in some such embodiments, ground electrode(s) 614 are omitted) in order to prevent accumulation of undesired ionic molecules in or near the retinas of the patient). In other embodiments, uniphasic or biphasic signals are applied between pairs of electrodes 111 wherein the current is applied between one electrode 111 near one eye (on, say, the left-hand disposable therapy strip 615) and one electrode 111 near the other eye (on, say, the right-hand disposable therapy strip 615). In other embodiments, uniphasic or biphasic signals are applied between pairs of electrodes 111 wherein the current is applied between one electrode 111 and another electrode 111 on the same disposable therapy strip 615.

FIG. 6B is a plan-view diagram of a disposable set 660 of electrodes including a single semi-encircling strip disposable therapy strip 615 and a single "ground" electrode 641, according to some embodiments of the present invention. In some embodiments, two such sets 660 of electrodes are adhered to the patient 99 in the desired positions; then a controller unit 661 (e.g., mounted to a headband such as shown in FIG. 6A, or mounted to eyeglasses (such as in FIG. 4A, or mounted to a neck-mounted or other suitably positioned controller)) worn by patient 99 is electrically (and/or optically, in the case where optical fibers couple light from LEDs in the controller unit to emission points on therapy strip 615) connected to each unit of the sets 660 of electrodes. In some embodiments, electrode 641 is connected to the device by conductor cable 642. Some embodiments include a tab or connector unit located between parts of the controller 661 to allow for modular assembly and replacement of parts of the device.

Figure 7:
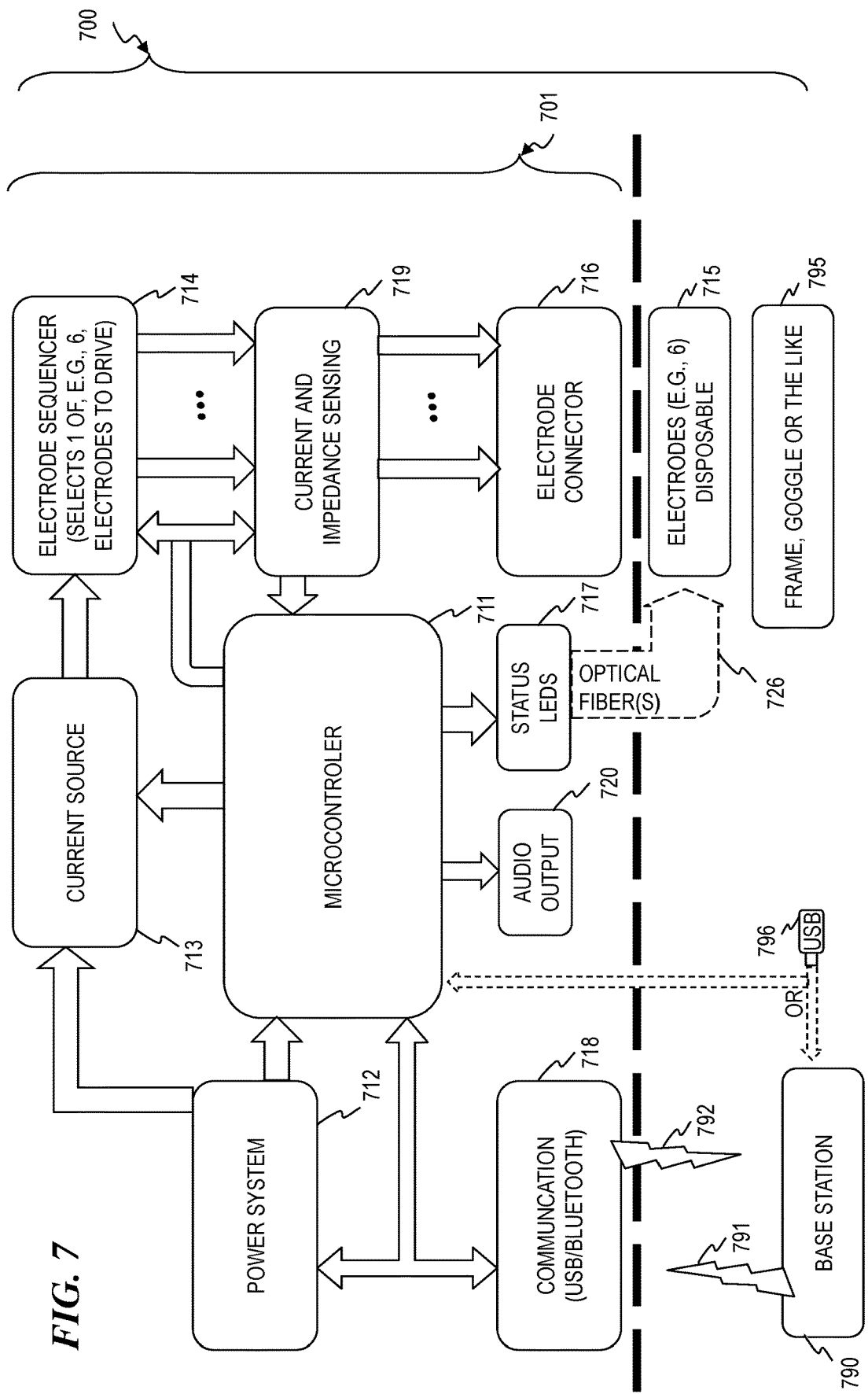
FIG. 7 is a schematic block diagram of a therapy system 700 including a controller 701 and electrodes 715, according to some embodiments of the present invention.

FIG. 7 is a schematic block diagram of a therapy system 700 including a controller 701 and electrodes 715, according to some embodiments of the present invention. In some embodiments, therapy system 700 includes base station 790, controller 701, FLASH drive 796, disposable electrodes 715, and (as needed) disposable ground patches, conductive gel and cleaning wipes. In some embodiments, base station 790 is a device, such as a laptop personal computer (PC), tablet computer, desktop computer or the like, for selecting parameters, monitoring performance, data collection and storage and communication with the control unit (controller 701). In some embodiments, controller 701 is a control unit that contains the electronics that deliver current to the electrode contacts on the eye. In some embodiments, the electrode contacts are part of a disposable strip, goggles or an individual probe or the like. In some embodiments, FLASH drive 796 is a USB "thumb drive" that includes encrypted data and program code to provide a fixed number of prepaid patient therapies, wherein each time a successful therapy is completed one therapy unit is deducted from the flash drive. In some embodiments, FLASH drive 796 is a USB "thumb drive" that includes encrypted data and program code to provide prescriptions for specific patient therapies, wherein each time a successful therapy is completed one therapy unit is deducted from the flash drive. In some embodiments, once all available therapy unit sessions are completed, the FLASH drive 796 can be discarded and a new prepaid flash drive is used. In other embodiments, the FLASH drive 796 is also used to gather and record session data and parameters that can be later analyzed to determine long-term effectiveness of various different therapy variations, so once all available therapy unit sessions are completed, the FLASH drive 796 is returned to the analysis facility and in exchange for the data and a per-therapy-session fee, a new prepaid flash drive is sent out to the treatment facility. In some embodiments, the patient identification data is anonymized and encrypted for patient privacy and/or legal requirements, while keeping each session with enough information to analyze what works and what does not work. In some embodiments, disposable electrodes 715 include a plurality of electrode contacts in the form of an adhesive strip, disposable handheld probe tip or goggle, that includes, for example, six to twelve contacts (or other suitable number), split with some on the upper eyelid portion and others on the lower eyelid portion. In some embodiments, a kit is provided wherein, in addition to the above-mentioned disposable electrodes 715 (contact strips), one or more handheld probe tips, and/or goggles and the flash drive, the kit also includes such items as disposable ground patches, conductive gel and cleaning wipes.

In some embodiments, controller 701 includes a microprocessor 711, a power system (such as a battery, ultracapacitor or the like) 712 that supplies electrical power to the rest of the controller 701, a current-source 713 that is controlled by microprocessor 711 based on signals from current and impedance sensor 719, an electrode sequencer 714 that selects, for example, which one of six possible electrodes to which to send the electrical pulse signal at any moment in time, as controlled by microprocessor 711, and these pulses are sent through electrode connector 716 to the set of electrodes 715. In some embodiments, the set of disposable electrodes 715 also includes one or more LEDs (e.g., such as 122 of FIG. 1D) embedded in or on the strip, wherein these LEDs are driven by electrical signals sent through connector 716 and provide a status and patient-feedback function to tell the medical-professional person and/or the patient that the system is functioning and active. In other embodiments, one or more status LEDs 717 are located in the controller 701 and emit light to indicate status directly from controller 701, and/or through optical fibers 726 or the like embedded in or on the strip to emission points on the electrode strip, wherein these LEDs 717 are driven by electrical signals from microprocessor 711 and, as described above, provide a status and patient-feedback function to tell the medical-professional person and/or the patient that the system is functioning and active. In some embodiments, a wireless communications device 718 (such as Bluetooth®, NFC, infrared optical communications, or the like) provides one-way or two-way communications to a base station 790. In some embodiments, base station 790, based on a prepaid therapy authorization from, e.g., FLASH drive 796, transmits 791 programming information specific for the particular patient, wherein the authorization optionally includes authorization based on a fee having been paid, as well as patient-specific therapy control information that has been customized for the particular identified patient to be treated this session based on a treatment regimen prescribed by an eye doctor or the like. In some embodiments, session parameters are communicated 792 back to the base station (with parameters such as the actual number, polarity, sequence and strength of pulses, the measured impedance and/or current, indicated patient discomfort, and the like). In some embodiments, system 701 includes a patient-activatable switch (e.g., on system 701 or via a separate handheld switch that is wirelessly or in wired communication with system 701) that the patient is instructed to press if and when the patient feels discomfort or concern, and upon activation of that switch, electrical output from system 701 or even the entire system 701 is immediately shut off, and/or the timing of the activation of the switch by the patient is recorded and transmitted in the communication 792 of parameters from the session. Thus, this feedback from the patient herself or himself, in some embodiments, is used to fully shut down the device (for patient comfort and peace-of-mind, as well as a further enhancement to patient safety just in case the current source 713 has a fault and is sending too much current), and is then correlated to a particular time or other aspect of the treatment to allow design of better therapy sessions in the future, and/or can be used to immediately terminate the session (wherein microcontroller 711 will immediately change all connections to "OFF" (or high impedance) to block any further current to the patient, and/or the entire system 701 is then (i.e., after storing the timestamp of the switch press by the patient) shut down and disconnected from power source (e.g., battery) 712. In some embodiments, system 701 and/or base station 790 include an audio-output unit 720 that provides a sound (beep, chime, ding, or the like) associated with therapy session status, to indicate, e.g., "ON/session starting," in therapy, an alert as to insufficient or inappropriate treatment, and "OFF/session ending."

In some embodiments, system 700 is a software-driven system that provides programmability of all parameters including frequency, waveform, current level, duration of therapy and number of "cycles" around the eye (wherein, in some embodiments, one cycle is the independent activation of each of the six to twelve electrode contacts). In some embodiments, these parameters are programmed during manufacturing, while in other embodiments, the parameters are programmed in the field by the clinician or a company representative. In some embodiments, modifications to the programming parameters and/or software (e.g., as customized by the prescription for the treatment protocol provided by a licensed medical professional for a specific identified patient) are stored in a plug-in storage device 796 (such as a USB FLASH storage device or the like) and the parameters and/or program and loaded (by plugging-in device 796) into base station 790 (and then transmitted 791 (e.g., wirelessly or by wired connection) to system 701 to be stored in the memory of microprocessor 711). In other embodiments, plug-in storage device 796 is plugged directly into system 701 to load and store the parameters and/or program into the memory of microprocessor 711 (in some such embodiments, the base station 790 is omitted, while in other embodiments, base station 790 is retained to provide the technician/medical professional with status of each session in real time). In some embodiments, base station 790 is used to provide the technician/medical professional with status of each session of a plurality of simultaneous patient sessions in real time (e.g., in some embodiments, a laptop computer used as base station 790 is programmed to provide a split-screen progress monitor (e.g., wherein the display screen is split into, e.g., quadrants if up to four patients were simultaneously treated) for a plurality of treatment sessions for each of a plurality of patients). In some embodiments, the software may also be modified remotely using the wireless connection to the base station 790. In some embodiments, a prescription for a treatment session (the protocol, parameters and the like for controlling current amount, pulse duration, inter-pulse spacing and how many pulses are to be sent and the like) for each individual patient is prepared and checked by a licensed professional, and this prescription is downloaded and/or stored in base station 790, or into USB device 796 along with the prepaid activation code to enable only authorized treatments for specific patients. In some embodiments, the software in base station 790 and/or the software in system 701 verifies the match between a specific patient's prescription associated with a specific identified patient and patient-identification information of the specific identified patient in order to verify that the correct prescription is used for that patient.

Some embodiments include a large memory in the system 701 and/or in the base station to capture and record all pertinent patient and clinic data, including the treatment protocol such as the number of pulses applied to each electrode, the amount of current, and all other relevant parameters of what the treatment session involved (including, for example, whether an actual or sham treatment session was provided to the particular patient). In some embodiments, the recorded data are stored in a permanent-memory portion of USB storage device 796 (e.g., using a portion of memory that allows only a single write operation that may be followed by many read operations, in order that the data are permanently stored and later available). In some embodiments, these data are collected remotely and summarized by company and/or clinic personnel. In some embodiments, data is summarized to provide comparisons between patients and clinics and may be used in research. Over time, this data will allow the company or analysis facility to optimize the design and the clinical protocol, thus improving outcomes.

Some embodiments provide greater current-drive capacity via current source 713, as well as better current and impedance measurements via sensor unit 719. This allows the system 701 to deliver greater, and more-carefully controlled, current levels that overcome any unexpected higher impedance levels. In some embodiments, apparatus 700 has a governor (e.g., current controller) to prevent delivery of more than 350 microamps (μA) to the patient during therapy. In some embodiments, base station 790 and/or system 701 may be activated only via an appropriately encoded message from flash drive 796, or via an authentic encrypted code (e.g., in some embodiments, received from a company website on the internet) that enables the laptop to signal, via WI-FI in some embodiments, the microstimulation controller 711 to conduct the therapy session for a particular identified patient. In some embodiments, the microstimulation controller 711 and system 701 is implemented on the goggle (e.g., unit 161 in FIG. 5A), and apparatus 701 may be activated via a flash drive 796 plugged into system 701 or by any other suitable type of connection (such as a USB cable to base station 790).

Some embodiments provide automatic adjustment to changes in impedance. As impedance changes during treatment, from contact to contact and from eye to eye, the control unit 701 will automatically adjust to maintain a consistent current level. This improves performance and outcomes. The treatment has been automated to minimize clinician involvement. The system 700 automatically manages the therapy to ensure uniform and repeatable results.

In some embodiments, the control unit 701 is designed to fit and connect nicely on the left and right ground patches (e.g., 641 of FIG. 6A). This eliminates the potential of losing signal to the left and right set of contacts due to patient movement during therapy. The small size of the control unit reduces clutter, improves patient comfort, and improves device consistency and compliance.

In some embodiments, the control unit is designed to be tamper proof (both physically and electronically), and to provide encryption on the programming and the sensed parameters to prevent hacking.

In some embodiments, the base station 790 communicates with the control unit 701 via a wireless connection eliminating the need to tether the patient to the base station. This improves compliance and makes the setup and therapy session easier to manage.

In some embodiments, the base station can communicate with multiple control units at one time reducing the number of base stations required, therefore reducing set-up time and the clinician's time to manage multiple patients.

In some embodiments, multiple levels of protection help ensure that the electrical current delivered to the contacts cannot exceed the programmed current. The design ensures that an unsafe level of current cannot be achieved even if the output was shorted (zero impedance). In some embodiments, the control unit 701 is powered by a small direct-current (DC) button cell and is not connected to the base station during therapy, reducing or eliminating the possibility of injury to the patient.

In some embodiments, the low cost of the design allows most or all of the system to be single-use and disposable.

In some embodiments, the base station can communicate with a device such as a goggle device and or strips partially or completely encircling the upper and or lower eyelids, as well as other body parts.

Figure 8:
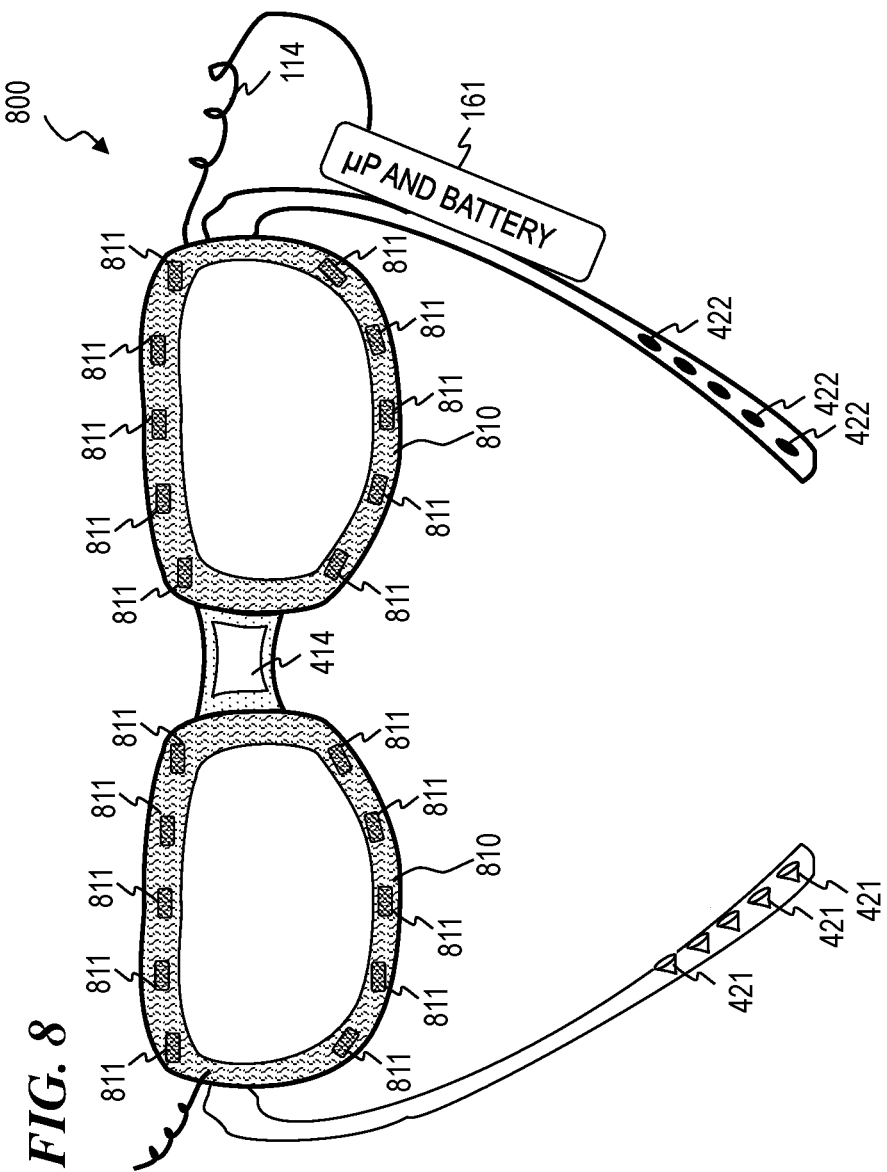
FIG. 8 is a schematic block diagram of a therapy system 800 including a controller 161 and light sensors 811, according to some embodiments of the present invention.

FIG. 8 is a schematic block diagram of a therapy system 800 including a controller 161 and a plurality of light sensors 811 mounted to an eyeglass frame or goggle-type fixture, according to some embodiments of the present invention. The other various reference numbers in FIG. 8 are as described above for FIG. 4A. In some embodiments, the plurality of light sensors 811 are used to sense the amount and/or direction of the ambient light in the room where the therapy is provided, and these data are recorded during some or all sessions, in order to determine whether or not ambient room light during the session makes any difference to the efficacy or effectiveness of treatment (i.e., this provides one additional parameter that is recorded, just in case the ambient light during the therapy session affects outcome and/or whether the patient feels less anxiety or boredom during therapy under differing ambient light conditions).

In some embodiments, the present invention includes combinations of two or more features that are individually and/or collectively shown and described above in FIG. 1A through FIG. 8. One non-limiting example of such a combination is to include one or more vibrators, and/or one or more LEDs and/or one or more electrode contact points in the goggle-type fixture of FIG. 8. In some other embodiments, the present invention provides subcombinations that include most features of the various embodiments, but omit one or more features that are individually shown and described above in FIG. 1A through FIG. 8.

Some embodiments of the present invention include a disposable therapy appliance that preferably includes a curved linear strip, semi-encircling strip, or encircling strip of material containing a plurality of electrodes for applying the microcurrent therapy, and optionally one or more sensors and/or other transducers. In some embodiments, the linear, semi-encircling, or encircling strip of material is positioned to place electrodes on the upper eye lid and the lower eye lid. In some embodiments, the curved linear, semi-encircling, or encircling strip of material includes a mild adhesive to make the strip adhere to the skin, and/or includes a conductive gel at the electrode contact points. Within or on the linear, semi-encircling, or encircling strip are electrodes spaced at specific points that are wired individually and separately to a controller apparatus that generates the prescribed microcurrent in a sequence to the plurality of electrode points on the material. In some embodiments, the microcurrent-stimulation controller apparatus to which the disposable therapy appliance is connected also contains a software system that is programmed to sequence the therapy to the various electrode points on the material, and to also detect electrical impendence from the patient, and thereby provide feedback to the controller apparatus to automatically adjust the level of microcurrent simulation, in order to deliver the amount of stimulation originally pre-selected for that treatment session by the clinician to achieve improved/optimum therapy.

In some embodiments, the disposable therapy appliance includes one or more "light-delivery" filaments threaded through or LEDs embedded in or on the strip material to convey a low level of light signal, indicating to the patient that the appliance/strip is functioning as intended. This low level of light signal is of a selected intensity and a selected spectrum chosen to penetrate the patient's closed eyelid and be received by those photoreceptor cells functioning in the back of the retina. In some embodiments, the light signal will resemble a dull flash or pulsating light, and may be either a white light or a specially colored light (such as red or green).

In some embodiments, the disposable therapy appliance includes a vibrating filament threaded through the strip or vibrator embedded in or on the strip material or simply connected to the strip, to convey a gentle level of vibration as the microcurrent stimulation therapy is being applied. Again, in some embodiments, this provides the function of conveying to the patient that the stimulation is being delivered for those instances where the electrostimulation of the microcurrent, itself, is simply unfelt by the patient. The benefit of this is that the patient can feel that the system is working, and the patient will then be more willing to sit still and complete the full treatment session, versus a session where the patient has no marker to indicate that anything is happening.

In some embodiments, the disposable therapy appliance is positioned and affixed to the patient by the attending physician or clinician in the clinic. The patient's eyelid is cleaned with sterile solution contained in a wipe or similar material. The clinician, using sterile surgical gloves, then opens the packet containing the disposable therapy appliance(s). In some embodiments, the disposable therapy strips have a crack-open, peel-off backing that is removed just prior to user. In some embodiments, the clinician then applies the strip(s) in the following manner:

A) For embodiments implemented as individual curved linear strips: a first strip is placed on the closed upper eyelid, below the eyebrow, across or beneath the bone of the upper eye orbit cavity. With the eye remaining closed, a second strip is then applied under the eye, along the bone of the lower orbit. If the patient's other eye is to be stimulated, then the individual strips for the second eye are prepared in the same fashion. Then, the strips are connected to the micro-current stimulation controller apparatus to initiate therapy.

B) For embodiments implemented as semi-circle strip: the top of the strip is placed on the closed eyelid, below the eyebrow, across the bone of the upper eye orbit cavity. With the eye remaining closed, the lower part of the strip-semicircle is then applied under the eye, along the bone of the lower orbit. If a second eye is to be stimulated, then the second eye is prepared in the same fashion with a second semi-circle strip. Then the strip(s) is/are connected to the micro-current stimulation controller apparatus to initiate therapy.

C) For embodiments implemented as circular strip: the top of the circular strip is placed on the closed eyelid, below the eyebrow, across the bone of the upper eye orbit cavity. With the eye remaining closed, the lower part of the circular strip is applied under the eye, along the bone of the lower orbit. If the patient's other eye is to be stimulated, then the second eye is prepared in the same fashion with a second circular strip. Then the strip or strips are connected to the micro-current stimulation controller apparatus to initiate therapy.

In some embodiments, when the therapy is finished, a beeper sounds, a light turns on or flashes, and/or other indication of completion is provided. The clinician then disconnects the strips from the micro-current stimulation controller apparatus generating the micro-current stimulation. The clinician then gently peels back the strips (from whatever configuration is used). The strips will be disposed of in accordance with company instructions as guided by any government directives. The patient's eye is re-cleansed with a sterile wipe or pad.

Advantages of the new technology of the present invention's micro-current stimulation curved linear strip, semi-encircling strip, or encircling strip include:

a. providing a novel electrode appliance for providing microcurrent stimulation therapy to a body part to combat chronic pain, injury, or disease in that body part;

b. providing a novel electrode appliance for treating various diseases, including macular degeneration and retinitis pigmentosa;

c. providing an electrode appliance that delivers micro-current stimulation therapy via a strip, semi-circle or circle of material containing a plurality of electrodes that are wired individually separately to the micro-current stimulation controller apparatus and are positioned to predetermined spaced-apart locations on the upper and/or lower eye lid with an adhesive material;

d. providing sensors to monitor the current supplied to the various points in the material and adjust the current based upon the degree of impedance of the patient's tissue;

e. providing curved linear strips, semi-encircling strips, or encircling strips or other shaped strips, semicircles or circles of material containing various numbers of electrodes that are disposable after each treatment session. In some embodiments, the invention is packaged in clean or sterile packaging, depending upon the requirements, in a barrier or contamination-proof package. The disposability reduces the risk of cross contamination between patients and eliminates the need to sterilize or clean a hand-held probe conventionally used by clinical professionals to treat patients.

f. optionally including one or more light filaments that can signal to the patient during the therapy session that the proper level of therapy is being delivered to the patient and that they are not experiencing undue impedance.

g. incorporating a safety feature by separately wiring each electrode or sensor to the treatment device that provides the electrical stimulation. Such a design prevents more than one electrode delivering the therapy simultaneously and potentially injuring the patient;

h. that the stimulation is not carried simultaneously over the entire surface of the treatment strip or semi-circle or circle but is concentrated at specific individual spaced-apart sites;

i. determining specific areas of stimulation by the software program of the apparatus connected to the micro-current strip, circle or semi-circle. The microcurrent strip, circle or semi-circle has specifically located points within the material that can deliver timed or sequenced specific stimulation to different points along the material, in a pre-set sequence, for a varied or pre-set time, at an individual point of contact, or at two or more points of individual contact, with preset stimulation levels, as opposed to a large pad which offers blanket stimulation over the entire surface area of the pad.

j. enabling the physician, using the therapy appliance and its treatment methodology, to target stimulation to a particular treatment point (in some embodiments, as small as 1-2 millimeters, or as large as 5-10 millimeters), which improves treatment efficacy since a higher current dose cannot be tolerated by the body at a small pinpoint of delivery, or be effective if delivered over a larger surface area, such as by a standard gel pad. Further, this stimulation can be delivered to a specifically designed and tolerated treatment point within a timed sequence and then on to another in a pre-set pattern designed to optimize treatment results for patients.

Details in some embodiments of the disposable adhesive appliances include one or more of the following:

a) Application to upper, and/or lower eye, as well as other body parts.
b) Microstimulation curved linear strips, semi-encircling strips, or encircling strips is disposable packaged sterile or clean
c) Microstimulation curved linear strips, semi-encircling strips, or encircling strips is gel coated and with perimeter adhesive
d) Microstimulation curved linear strips, semi-encircling strips, or encircling strips contains unique contact points that:
   i. have between 2-10 contact points on each curved linear strip;
   ii. have between 2-20 contact points on semi-encircling strips, or encircling strips;
   iii. does not stimulate entire set of electrodes on a pair of curved linear strips, semi-encircling strips, or encircling strips; only specific points selected within the stimulation program determined by physician and programmed into the apparatus;
   iv. Contact points can be activated individually (one-at-a-time) or multiple points at a time; meaning that in some embodiments, only one contact point can stimulate at a time per eye, or body part; OR in other embodiments, two or more contact points may stimulate simultaneously, determined by the program mode selected on the apparatus. However, the entirety of the strip or semi-circle or circle is not active with stimulation at any one given point in time;
   v. Contact points can be sequenced, in a pattern that is pre-set and determined by the program of the apparatus delivering the stimulation;
   vi. Contact points are capable of receiving varied stimulation levels as determined by the apparatus, meaning that the stimulation level delivered through the various contact points can vary and be increased or decreased throughout the course of the treatment program selected either as determined by the apparatus or by the physician.
e) Safety Element: Strips rely on a safety governor built in to the device (apparatus) so one point cannot deliver more than 350 mA current. Strips have a built-in sensor to monitor the stimulation level delivered in order to improve treatment performance. In some embodiments, the sensor also gauges impedance at the site of stimulation and adjusts current through a feedback loop.
f) Strips contain a light filament built in to indicate stimulation delivery.
g) Strips contain a vibration element designed to indicate stimulation delivery.
h) Strips contain a connection element to primary device.

In some embodiments, the present invention provides an apparatus that includes: a disposable therapy appliance, wherein the disposable therapy appliance includes: a strip of material containing a plurality of electrodes configured to apply microcurrent stimulation therapy to a patient, wherein each electrode is no larger than 25 mm$^2$, and wherein the strip is shaped to be positioned to place electrodes on an upper eyelid and a lower eyelid of a the patient's skin, and wherein each one of the plurality of electrodes is configured to be individually activated at a time for microcurrent stimulation without activation of any other ones of the plurality of electrodes during that time.

In some embodiments of the apparatus, the strip of material includes an adhesive suitable to adhere the strip adhere to the skin.

In some embodiments of the apparatus, the strip of material includes an amount of conductive gel on a skin-contact point of each one of the plurality of electrodes, and the apparatus further includes a removable protective layer that separately encloses each amount of conductive gel such that the amounts of conductive gel do not touch each other when the strip is applied to the patient's skin.

Some embodiments of the apparatus further include a microcurrent-stimulation controller, wherein the electrodes are spaced at predetermined location points along the strip of material, and are wired individually and separately to the microcurrent-stimulation controller, and wherein the microcurrent-stimulation controller generates a prescribed microcurrent delivered to each electrode of the plurality of electrodes in a temporal sequence. In some such embodiments, the microcurrent-stimulation controller apparatus contains a software system that is programmed to sequence the therapy to the plurality of electrodes, and to also detect electrical impedance between the electrodes and the patient, and thereby provide feedback to the controller to automatically adjust the level of microcurrent simulation, in order to deliver the amount of stimulation originally pre-selected for that treatment session by the clinician to achieve improved/optimum therapy. In some embodiments, the microcurrent-stimulation controller apparatus includes a current controller circuit operative to control an amount of current; the microcurrent-stimulation controller apparatus includes a current sensing circuit operative to provide a first feedback signal indicative of the amount of current delivered to one of the plurality of electrodes; and the software system in the microcurrent-stimulation controller apparatus adjusts the current controller circuit based on the first feedback signal and on the set of parameters selected for the patient. In some embodiments, the microcurrent-stimulation controller apparatus includes a patient-activatable switch, and wherein the microcurrent-stimulation controller apparatus is configured to stop therapy upon activation of the switch. In some embodiments, the microcurrent-stimulation controller apparatus includes a patient-activatable switch, and wherein the microcurrent-stimulation controller apparatus is configured to record a timestamp associated with activation of the switch. In some embodiments, the microcurrent-stimulation controller apparatus is configured to visibly show status of the treatment session. In some embodiments, the microcurrent-stimulation controller apparatus is configured to capture data parameters of the treatment session and to transmit the captured data to a base station for analysis to refine later treatment sessions and to confirm the apparatus is working properly and being administered properly, and to ensure consistency of results. In some embodiments, the microcurrent-stimulation controller apparatus is configured to adjust protocol for a treatment session in a clinic via the software system based on a received WIFI signal. In some embodiments, the microcurrent-stimulation controller apparatus is configured to adjust protocol for a treatment session in a clinic via the software system based on a signal received from a remote system via the internet. In some embodiments, the microcurrent-stimulation controller apparatus is configured to adjust protocol for a treatment session based on data received from a USB-connected storage device directly connected to the microcurrent-stimulation controller apparatus. In some embodiments, the microcurrent-stimulation controller apparatus is configured to adjust protocol for a treatment session based on data wirelessly received from a base station having a USB-connected storage device directly connected to the base station.

Some embodiments of the apparatus further include a vibrator connected to the strip to convey a gentle level of vibration as the microcurrent stimulation therapy is being applied.

Some embodiments of the apparatus further include at least one light emitter device on the strip. In some such embodiments, the strip is transparent or translucent such that light from the at least one light emitter device is visible to both the patient and to an outside observer.

Some embodiments of the apparatus further include a plurality of light emitter devices on the strip, wherein each respective one of the plurality of electrodes has an associated one of the plurality of light emitter devices in a vicinity of the respective electrode; and a microcurrent-stimulation controller, wherein the electrodes spaced at predetermined location points along the strip of material, and are wired individually and separately to the microcurrent-stimulation controller, wherein the microcurrent-stimulation controller generates a prescribed microcurrent pulse delivered to each electrode of the plurality of electrodes in a temporal sequence, and wherein the microcurrent-stimulation controller activates the respective associated one of the plurality of light emitter devices during the delivered microcurrent pulse to the respective electrode. In some such embodiments, the microcurrent-stimulation controller is configured to receive activation data from a USB storage device, and wherein the activation data is encrypted, and wherein the encrypted activation data is required to be received by the microcurrent-stimulation controller before a microcurrent stimulation therapy session is initiated.

In some embodiments of the apparatus, the strip of material includes an adhesive suitable to adhere the strip to a goggle device; and the apparatus further includes the goggle device, wherein the goggle device is shaped to hold the plurality of electrodes against the patient's skin without any adhesive touching the patient's skin. In some such embodiments, the apparatus further includes a vibrator connected to the goggle device to convey a gentle level of vibration as the microcurrent stimulation therapy is being applied.

In some embodiments, the present invention provides a method that includes: providing a disposable strip of material containing a plurality of electrodes configured to apply microcurrent stimulation therapy to a patient, wherein each electrode is no larger than 25 mm$^2$, and wherein the strip is shaped to be positioned to place electrodes on an upper eyelid and a lower eyelid of the patient's skin, wherein the electrodes are spaced at predetermined location points along the strip of material, and wherein each one of the plurality of electrodes is configured to be individually activated at a time for microcurrent stimulation without activation of any other ones of the plurality of electrodes during that time; providing a microcurrent-stimulation controller, wherein the electrodes are wired individually and separately to the microcurrent-stimulation controller; applying the disposable strip of material to the patient's skin; generating prescribed microcurrent pulses by the microcurrent-stimulation controller; and delivering the microcurrent pulses to each respective electrode of the plurality of electrodes in a temporal sequence.

In some embodiments of the method, the strip of material includes a pressure-sensitive adhesive suitable to adhere the strip adhere to the skin, and wherein the applying the disposable strip of material to the patient's skin includes contacting the adhesive to the patient's skin.

In some embodiments of the method, the strip of material includes an amount of conductive gel on a skin-contact point of each one of the plurality of electrodes, and a removable protective layer that separately encloses each amount of conductive gel such that the amounts of conductive gel do not touch each other when the strip is applied to the patient's skin.

Some embodiments of the method further include sequencing the therapy to the plurality of electrodes under software control; detecting electrical impedance between the electrodes and the patient; and providing feedback to automatically adjust a level of microcurrent simulation, in order to deliver the amount of stimulation originally pre-selected for that treatment session to achieve improved and/or optimum therapy.

Some embodiments of the method further include conveying a gentle level of vibration as the microcurrent stimulation therapy is being applied.

Some embodiments of the method further include emitting light from the strip. Some embodiments of the method further include emitting light from the rim of a pair of goggles or the frame of a pair of eyeglasses, wherein the goggles hold the strip against the patient's skin, and wherein the light is visible to the patient through the strip.

Some embodiments of the method further include emitting light from a plurality of light-emitting locations on the strip, wherein each light-emitting location is in a vicinity of an associated respective one of the plurality of electrodes; and wherein the emitting light from the respective associated one of the plurality of light-emitting locations is during the delivering of the microcurrent pulse to the respective electrode. Some embodiments of the method further include emitting light from a plurality of locations on the rim of a pair of goggles or the frame of a pair of eyeglasses, wherein the goggles hold the strip against the patient's skin, and wherein the light is visible to the patient through the strip coming from the plurality of locations.

Some embodiments of the method further include receiving activation data from a USB storage device, and wherein the activation data is encrypted, and wherein the encrypted activation data is required to be received before a microcurrent stimulation therapy session is initiated. In some such embodiments, the activation data includes identification of a particular patient and a prescription that includes parameters that control a therapy session for that particular patient. In some such embodiments, the activation data includes payment information for a particular patient. In some such embodiments, the activation data includes payment information for a predetermined number of therapy sessions.

Some embodiments of the method further include receiving activation data from a USB storage device, and wherein the activation data is not encrypted, and wherein the non-encrypted activation data is required to be received before a microcurrent stimulation therapy session is initiated.

In some embodiments of the method, the applying of the disposable strip of material to the patient's skin includes adhering the strip to a goggle device shaped to hold the plurality of electrodes against the patient's skin without any adhesive touching the patient's skin.

Some embodiments of the method further include conveying a gentle level of vibration as the microcurrent stimulation therapy is being applied.

In some embodiments, the present invention provides an apparatus that includes: a disposable strip of material containing a plurality of electrodes configured to apply microcurrent stimulation therapy to a patient, wherein each electrode is no larger than 25 mm², and wherein the strip is shaped to be positioned to place electrodes on an upper eyelid and a lower eyelid of the patient's skin, wherein the electrodes are spaced at predetermined location points along the strip of material, and wherein each one of the plurality of electrodes is configured to be individually activated at a time for microcurrent stimulation without activation of any other ones of the plurality of electrodes during that time; means for applying the disposable strip of material to the patient's skin such that each one of the plurality of electrodes is in electrical communication with the patient's skin; means for generating prescribed microcurrent pulses; and means for delivering the microcurrent pulses to each respective electrode of the plurality of electrodes in a temporal sequence. In some embodiments, the strip of material includes a pressure-sensitive adhesive suitable to adhere the strip adhere to the skin, and wherein the means for applying the disposable strip of material to the patient's skin includes means for contacting the adhesive to the patient's skin. In some embodiments, the strip of material includes an amount of conductive gel on a skin-contact point of each one of the plurality of electrodes, and removable means for separately enclosing each amount of conductive gel such that the amounts of conductive gel do not touch each other when the strip is applied to the patient's skin. Some embodiments further include means for sequencing the therapy to the plurality of electrodes under software control; means for detecting electrical impedance between the electrodes and the patient; and means for providing feedback to automatically adjust a level of microcurrent simulation, in order to deliver the amount of stimulation originally pre-selected for that treatment session to achieve improved and/or optimum therapy. Some embodiments further include means for conveying a gentle level of vibration as the microcurrent stimulation therapy is being applied. Some embodiments further include means for emitting light from the strip. Some embodiments further include means for emitting light from a plurality of light-emitting locations on the strip, wherein each light-emitting location is in a vicinity of an associated respective one of the plurality of electrodes; and wherein the means for emitting light from the respective associated one of the plurality of light-emitting locations emits light during the delivering of the microcurrent pulse to the respective electrode.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. A method comprising:
   providing a first electrode substrate, wherein the first electrode substrate includes:
   a first plurality of electrodes on the first electrode substrate that are configured to apply tissue-stimulation electrical-current therapy to a first eye of a patient, the first eye having an upper eyelid and a lower eyelid, wherein the first electrode substrate is configured to locate the first plurality of electrodes on an outer surface of at least one of the upper eyelid and the lower eyelid of the patient's first eye, and wherein each one of the first plurality of electrodes is configured to be individually activated, and
   attaching the first electrode substrate to the patient's skin such that the first plurality of electrodes are on the outer surface at least one of the upper eyelid and the lower eyelid of the patient's first eye;
   applying the tissue-stimulation electrical-current therapy to the first eye;
   providing sensors; and
   sensing, using the sensors, electrical signals of a nerve from the patient's eyelid skin that indicate patient discomfort, wherein the applying of the tissue-stimulation therapy to the first eye of the patient is adjusted based on the sensed nerve electrical signals from the patient's eyelid skin.

2. The method of claim 1, where the attaching of the first electrode substrate to the patient's skin includes locating one or more the first plurality of electrodes on an outer surface of the patient's upper eyelid and one or more of the first plurality of electrodes on an outer surface of the patient's lower eyelid.

3. The method of claim 1, wherein the first electrode substrate further includes at least one LED on the first electrode substrate, the method further comprising:
   activating the at least one LED to indicate a status of the tissue-stimulation electrical-current therapy.

4. The method of claim 1, wherein the first electrode substrate further includes at least one LED on the first electrode substrate, wherein the applying of the tissue-stimulation electrical-current therapy occurs during a treatment session, the method further comprising:
   activating the at least one LED to indicate how much time is remaining in the treatment session.

5. A non-transitory computer-readable medium having instructions stored thereon for causing a suitably programmed control system to execute a method of providing a tissue-stimulation electrical-current therapy to a first eye of a patient, the first eye having an upper eyelid and a lower eyelid, wherein the method is executed by the control system on a tissue-stimulation system that includes a first plurality of electrodes, and sensors, wherein the first plurality of electrodes are on a first electrode substrate, wherein the first electrode substrate is attached to the patient's skin such that the first plurality of electrodes are on the outer surface at least one of the upper eyelid and the lower eyelid of the patient's first eye, and wherein each one of the first plurality of electrodes is configured to be individually activated, the method comprising:
   applying the tissue-stimulation electrical-current therapy to the first eye; and
   sensing, using the sensors under the control of the control system, electrical signals of a nerve from the patient's eyelid skin that indicate patient discomfort, wherein the applying of the tissue-stimulation therapy to the first eye of the patient is adjusted based on the sensed nerve electrical signals from the patient's eyelid skin.

6. The non-transitory computer-readable medium of claim 5, further comprising instructions such that the applying of the tissue-stimulation electrical-current therapy occurs during one or more treatment sessions, wherein each of the one or more treatment sessions has a protocol, the non-transitory computer-readable medium further comprising instructions such that the method further includes adjusting the protocol for a respective treatment session of the one or more treatment sessions based at least in part on sensed-signal data received by the control system.

7. The non-transitory computer-readable medium of claim 5, wherein the first electrode substrate further includes at least one LED on the first electrode substrate, the computer-readable medium further comprising instructions such that the method further comprises:
activating the at least one LED to indicate a status of the tissue-stimulation electrical-current therapy.

8. A system comprising:
a first electrode substrate that includes:
a first plurality of electrodes on the first electrode substrate that are configured to apply tissue-stimulation electrical-current therapy to a first eye of a patient, the first eye having an upper eyelid and a lower eyelid, wherein the first electrode substrate is configured to locate the first plurality of electrodes on an outer surface of at least one of the upper eyelid and the lower eyelid of the patient's first eye, and wherein each one of the first plurality of electrodes is configured to be individually activated;
a tissue-stimulation controller, wherein the tissue-stimulation controller is operatively coupled to apply the tissue-stimulation electrical-current therapy to the first eye; and
sensors operatively coupled to the tissue-stimulation controller and configured to sense electrical signals of a nerve from the patient's eyelid skin that indicate patient discomfort, wherein the tissue-stimulation therapy applied to the first eye of the patient is adjusted based on the sensed nerve electrical signals from the patient's eyelid skin.

9. The system of claim 8, wherein the first electrode substrate is configured to locate one or more the first plurality of electrodes on an outer surface of the patient's upper eyelid and one or more of the first plurality of electrodes on an outer surface of the patient's lower eyelid.

10. The system of claim 8, further comprising:
a second electrode substrate that includes:
a second plurality of electrodes on the second electrode substrate that are configured to apply the tissue-stimulation electrical-current therapy to a second eye of the patient, the second eye having an upper eyelid and a lower eyelid, wherein the second electrode substrate is configured to locate the second plurality of electrodes on an outer surface of at least one of the upper eyelid and the lower eyelid of the patient's second eye, and wherein each one of the second plurality of electrodes is configured to be individually activated; and
wherein the tissue-stimulation controller is operatively coupled to provide the tissue-stimulation electrical-current therapy to the second eye through control of at least one of the second plurality of electrodes.

11. The system of claim 8, wherein the first electrode substrate further includes at least one LED on the first electrode substrate, and wherein the tissue-stimulation controller is configured to activate the at least one LED to indicate a status of the tissue-stimulation electrical-current therapy.

12. The system of claim 8, wherein the first electrode substrate further includes at least one LED on the first electrode substrate, wherein the tissue-stimulation electrical-current therapy is applied to the patient according to one of a plurality of selectable therapy protocols, and wherein the tissue-stimulation controller is configured to activate the at least one LED to indicate which therapy protocol of the plurality of therapy protocols is being applied.

13. The system of claim 8, wherein the first electrode substrate further includes at least one LED on the first electrode substrate, and wherein the tissue-stimulation electrical-current therapy is applied to the patient during a treatment session, and wherein the tissue-stimulation controller is configured to activate the at least one LED to indicate how much time is remaining in the treatment session.

14. The system of claim 8, wherein the first electrode substrate further includes at least one LED on the first electrode substrate, and wherein the first electrode substrate is configured such that light from the at least one LED is visible to the patient.

15. The system of claim 8, wherein the first electrode substrate further includes at least one LED on the first electrode substrate, and wherein the first electrode substrate is configured such that light from the at least one LED is visible to both the patient and to an outside observer.

16. The system of claim 8, further comprising:
a vibrator connected to the first electrode substrate to apply vibration to the patient as the tissue-stimulation electrical-current therapy is being applied.

17. The system of claim 8, wherein the first electrode substrate further includes at least one LED on the first electrode substrate, and wherein the first electrode substrate is configured such that light from the at least one LED is visible to both the patient and to an outside observer, the system further comprising:
a vibrator connected to the first electrode substrate to apply vibration to the patient as the tissue-stimulation electrical-current therapy is being applied.

18. The system of claim 8, wherein the tissue-stimulation electrical-current therapy is applied to the first eye during one or more treatment sessions, wherein each of the one or more treatment sessions has a protocol, and wherein the tissue-stimulation controller is configured to adjust the protocol for a respective treatment session of the one or more treatment sessions based at least in part on sensed-signal data received by the tissue-stimulation controller.

19. The system of claim 8, wherein the tissue-stimulation electrical-current therapy is applied to the first eye during a plurality of treatment sessions including a first treatment session and a second treatment session, wherein each one of the plurality of treatment sessions has a protocol, and wherein the tissue-stimulation controller is configured to adjust the protocol for the second treatment session based at least in part on discomfort feedback from the patient received during the first treatment session.

20. The system of claim 8, wherein the tissue-stimulation controller includes a patient-activatable switch, and wherein the tissue-stimulation controller is configured to stop the tissue-stimulation electrical-current therapy upon activation of the patient-activatable switch.

* * * * *